United States Patent [19]
Duggan et al.

[11] Patent Number: 5,952,341
[45] Date of Patent: Sep. 14, 1999

[54] INTEGRIN ANTAGONISTS

[75] Inventors: Mark E. Duggan, Schwenksville; George D. Hartman, Lansdale, both of Pa.

[73] Assignee: Merck & Co., Inc., Rahway, N.J.

[21] Appl. No.: 08/960,032

[22] Filed: Oct. 28, 1997

Related U.S. Application Data

[60] Provisional application No. 60/027,867, Oct. 30, 1996.

[51] Int. Cl.$^6$ .................. A61K 31/435; C07D 471/04
[52] U.S. Cl. ................. 514/300; 514/318; 514/357; 546/122; 546/193; 546/337
[58] Field of Search .................... 546/122, 193, 546/337; 514/300, 318, 357

[56] References Cited

U.S. PATENT DOCUMENTS

| | | | |
|---|---|---|---|
| 5,260,277 | 11/1993 | McKenzie | 544/18 |
| 5,391,466 | 2/1995 | Ueda et al. | 430/393 |
| 5,455,243 | 10/1995 | Duggan et al. | 514/218 |
| 5,534,524 | 7/1996 | Bonewald et al. | 514/314 |
| 5,665,358 | 9/1997 | Barton et al. | 424/179.1 |
| 5,668,159 | 9/1997 | Jin et al. | 514/363 |
| 5,674,965 | 10/1997 | Carey et al. | 528/27 |
| 5,763,408 | 6/1998 | Nishikawa et al. | 562/560 |

FOREIGN PATENT DOCUMENTS

| | | |
|---|---|---|
| 2199923 | 9/1997 | Canada. |
| WO 95/32710 | 12/1995 | WIPO. |
| WO 97/26250 | 7/1997 | WIPO. |

OTHER PUBLICATIONS

Fujii et al., Chemical Abstracts, vol. 128, abstract 278737, 1998.
Bihovsky et al., Chemical Abstracts, vol. 123, abstract 56535, 1995.
Seitz et al., Chemical Abstracts, vol. 123, abstract 257291, 1995.
Ali et al., Chemical Abstracts, vol. 118, abstract 7397, 1993.
Alig et al., Chemical Abstracts, vol. 116, abstract 129634, 1992.
Zablocki et al., J. Med. Chem. (1995), vol. 38, pp. 2378–2394, "Potent in vitro and in vivo inhibitors of platelet aggregation based upon the Arg–Gly–Asp sequence of fibrinogen."
Rico et al., J. Org. Chem. (1993), vol. 58, pp. 7948–7951, "A highly stereoselective michael addition to an $\alpha$, $\beta$–unsaturated ester as the crucial step in the synthesis . . . ".

*Primary Examiner*—Richard L. Raymond
*Attorney, Agent, or Firm*—Philippe L. Durette; Anthony D. Sabatelli; Melvin Winokur

[57] ABSTRACT

This invention relates to certain novel compounds and derivatives thereof, their synthesis, and their use as vitronectin receptor antagonists. The vitronectin receptor antagonist compounds of the present invention are $\alpha v \beta 3$ antagonists, $\alpha v \beta 5$ antagonists or dual $\alpha v \beta 3/\alpha v \beta 5$ antagonists useful for inhibiting bone resorption, treating and preventing osteoporosis, and inhibiting restenosis, diabetic retinopathy, macular degeneration, angiogenesis, atherosclerosis, inflammation and tumor growth.

23 Claims, No Drawings

INTEGRIN ANTAGONISTS

CROSS-REFERENCE TO RELATED APPLICATIONS

The present invention is related to U.S. provisional applications Serial No. 60/027,867, filed Oct. 30, 1996, the contents of which are hereby incorporated by reference.

FIELD OF THE INVENTION

The present invention provides novel compounds and derivatives thereof, their synthesis, and their use as vitronectin receptor ligands. More particularly, the compounds of the present invention are $\alpha v\beta 3$ antagonists, $\alpha v\beta 5$ antagonists or dual $\alpha v\beta 3/\alpha v\beta 5$ antagonists useful for inhibiting bone resorption, treating and preventing osteoporosis, and inhibiting vascular restenosis, diabetic retinopathy, macular degeneration, angiogenesis, atherosclerosis, inflammation and tumor growth.

BACKGROUND OF THE INVENTION

This invention relates to compounds for inhibiting bone resorption that is mediated by the action of a class of cells known as osteoclasts.

Osteoclasts are multinucleated cells of up to 400 $\mu$m in diameter that resorb mineralized tissue, chiefly calcium carbonate and calcium phosphate, in vertebrates. They are actively motile cells that migrate along the surface of bone. They can bind to bone, secrete necessary acids and proteases and thereby cause the actual resorption of mineralized tissue from the bone.

More specifically, osteoclasts are believed to exist in at least two physiological states. In the secretory state, osteoclasts are flat, attach to the bone matrix via a tight attachment zone (sealing zone), become highly polarized, form a ruffled border, and secrete lysosomal enzymes and protons to resorb bone. The adhesion of osteoclasts to bone surfaces is an important initial step in bone resorption. In the migratory or motile state, the osteoclasts migrate across bone matrix and do not take part in resorption until they attach again to bone.

Integrins are transmembrane, heterodimeric, glycoproteins which interact with extracellular matrix and are involved in osteoclast attachment, activation and migration. The most abundant integrin in osteoclasts (rat, chicken, mouse and human) is the vitronectin receptor, or $\alpha v\beta 3$, thought to interact in bone with matrix proteins that contain the RGD sequence. Antibodies to $\alpha v\beta 3$ block bone resorption in vitro indicating that this integrin plays a key role in the resorptive process. There is increasing evidence to suggest that $\alpha v\beta 3$ ligands can be used effectively to inhibit osteoclast mediated bone resoption in vivo in mammals.

The current major bone diseases of public concern are osteoporosis, hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment.

All these conditions are characterized by bone loss, resulting from an imbalance between bone resorption (breakdown) and bone formation, which continues throughout life at the rate of about 14% per year on the average. However, the rate of bone turnover differs from site to site, for example, it is higher in the trabecular bone of the vertebrae and the alveolar bone in the jaws than in the cortices of the long bones. The potential for bone loss is directly related to turnover and can amount to over 5% per year in vertebrae immediately following menopause, a condition which leads to increased fracture risk.

There are currently 20 million people with detectable fractures of the vertebrae due to osteoporosis in the United States. In addition, there are 250,000 hip fractures per year attributed to osteoporosis. This clinical situation is associated with a 12% mortality rate within the first two years, while 30% of the patients require nursing home care after the fracture.

Individuals suffering from all the conditions listed above would benefit from treatment with agents which inhibit bone resorption.

Additionally, $\alpha v\beta 3$ ligands have been found to be useful in treating and/or inhibiting restenosis (recurrence of stenosis after corrective surgery on the heart valve), atherosclerosis, diabetic retinopathy, macular degeneration and angiogenesis (formation of new blood vessels). Moreover, it has been postulated that the growth of tumors depends on an adequate blood supply, which in turn is dependent on the growth of new vessels into the tumor; thus, inhibition of angiogenesis can cause tumor regression in animal models. (See, *Harrison's Principles of Internal Medicine*, 12th ed., 1991). $\alpha v\beta 3$ antagonists, which inhibit angiogenesis, are therefore useful in the treatment of cancer for inhibiting tumor growth. (See e.g., Brooks et al., *Cell*, 79:1157–1164 (1994)).

Moreover, compounds of this invention can also inhibit neovascularization by acting as antagonists of the integrin receptor $\alpha v\beta 5$. A monoclonal antibody for $\alpha v\beta 5$ has been shown to inhibit VEGF-induced angiogenesis in rabbit cornea and the chick chorioallantoic membrane model; M. C. Friedlander, et.al., *Science* 270, 1500–1502, 1995. Thus, compounds that antagonize $\alpha v\beta 5$ are useful for treating and preventing macular degeneration, diabetic retinopathy, and tumor growth.

In addition, certain compounds of this invention antagonize both the $\alpha v\beta 3$ and $\alpha v\beta 5$ receptors. These compounds, referred to as "dual $\alpha v\beta 3/\alpha v\beta 5$ antagonists," are useful for inhibiting bone resorption, treating and preventing osteoporosis, and inhibiting vascular restenosis, diabetic retinopathy, macular degeneration, angiogenesis, atherosclerosis, inflammation and tumor growth.

It is an object of the present invention to identify compounds which bind to the $\alpha v\beta 3$ receptor, $\alpha v\beta 5$ receptor or both the $\alpha v\beta 3$ and $\alpha v\beta 5$ receptors.

It is a further object of the invention to identify compounds which act as antagonists of the $\alpha v\beta 3$ receptor. It is another object of the invention to identify $\alpha v\beta 3$ antagonist compounds which are useful agents for inhibiting: bone resorption mediated by osteoclast cells, restenosis, atherosclerosis, inflammation, diabetic retinopathy, macular degeneration and angiogenesis in animals, preferably mammals, especially humans. Still another object of the invention is to identify $\alpha v\beta 3$ antagonists which cause tumor regression and/or inhibit tumor growth in animals.

A further object of the invention is to identify $\alpha v\beta 3$ antagonists useful for preventing or treating osteoporosis. An additional object of the invention is to identify $\alpha v\beta 3$ antagonists useful for treating cancer.

It has now been found that the compounds of the present invention, $\alpha v\beta 3$ ligands, are useful for inhibiting bone resorption in mammals. Thus, the compounds of the present invention are useful for preventing or reducing the incidence of osteoporosis. Additionally, the $\alpha v\beta 3$ ligands of the present invention are also useful for treating and/or inhibiting restenosis, diabetic retinopathy, macular degeneration, atherosclerosis and/or angiogenesis in mammals.

SUMMARY OF THE INVENTION

The present invention provides a compound of the formula

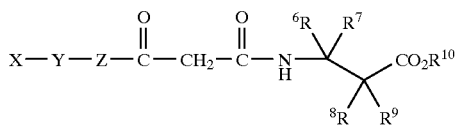

wherein X is selected from

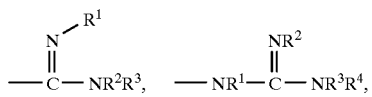

a 5- or 6-membered monocyclic aromatic or nonaromatic ring system containing 0, 1, 2, 3 or 4 heteroatoms selected from N, O or S wherein the 5- or 6-membered ring system is either unsubstituted or substituted with $R^1$ and $R^2$, or a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted with $R^1$ and $R^2$;

Y is selected from

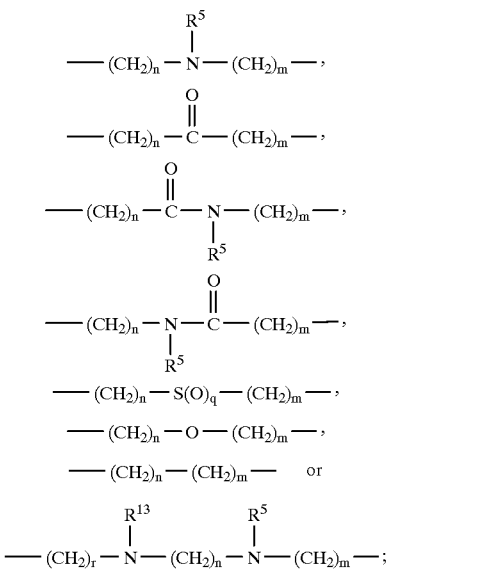

Z is absent or is a 4–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^{14}$, $R^{15}$, $R^{16}$ and $R^{17}$; preferably, Z is not a 6-membered monocyclic aromatic ring system;

$R^1$, $R^2$, $R^3$, $R^4$, $R^5$, $R^{11}$, $R^{12}$, $R^{13}$, $R^{16}$ and $R^{17}$ are each independently selected from
hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy or hydroxy $C_{1-6}$ alkyl;

$R^6$, $R^7$, $R^{14}$ and $R^{15}$ are each independently selected from
hydrogen,
aryl,
halogen,
aryl-$(CH_2)_p$—,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
$HC\equiv C(CH_2)_r$—
$C_{1-6}$ alkyl-$C\equiv C(CH_2)_r$—,
$C_{3-7}$ cycloalkyl-$C\equiv C(CH_2)_r$—,
aryl-$C\equiv C(CH_2)_r$—,
$C_{1-6}$ alkylaryl-$C\equiv C(CH_2)_r$—,
$H_2C=CH(CH_2)_r$—,
$C_{1-6}$ alkyl-$CH=CH(CH_2)_r$—,
$C_{3-7}$ cycloalkyl-$CH=CH(CH_2)_r$—,
aryl-$CH=CH(CH_2)_r$—,
$C_{1-6}$ alkylaryl-$CH=CH(CH_2)_r$—,
$C_{1-6}$ alkyl-$SO_2(CH_2)_r$—,
$C_{1-6}$ alkylaryl-$SO_2(CH_2)_r$—,
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl, aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl, or
aryl $C_{1-8}$ alkylaminocarbonyl $C_{1-6}$ alkyl,
wherein any of the alkyl groups may be unsubstituted or substituted with $R^{11}$ and $R^{12}$; and provided that the carbon atom to which $R^6$ and $R^7$ are attached is itself attached to no more than one heteroatom; or $R^6$ and $R^7$, or $R^{14}$ and $R^{15}$ are combined to form oxo, in which case the carbon atom to which $R^6$ and $R^7$ are attached can itself be attached to more than one heteroatom;

$R^8$ and $R^9$ are each independently selected from
hydrogen,
aryl,
halogen,
aryl-$(CH_2)_p$—,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
$HC{\equiv}C(CH_2)_r$—
$C_{1-6}$ alkyl-$C{\equiv}C(CH_2)_r$—,
$C_{3-7}$ cycloalkyl-$C{\equiv}C(CH_2)_r$—,
aryl-$C{\equiv}C(CH_2)_r$—,
$C_{1-6}$ alkylaryl-$C{\equiv}C(CH_2)_r$—,
$H_2C{=}CH(CH_2)_r$—,
$C_{1-6}$ alkyl-$CH{=}CH(CH_2)_r$—,
$C_{3-7}$ cycloalkyl-$CH{=}CH(CH_2)_r$—,
aryl-$CH{=}CH(CH_2)_r$—,
$C_{1-6}$ alkylaryl-$CH{=}CH(CH_2)_r$—,
$C_{1-6}$ alkyl-$SO_2(CH_2)_r$—,
$C_{1-6}$ alkylaryl-$SO_2(CH_2)_r$—,
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl, $C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl,
aryl $C_{1-8}$ alkylaminocarbonyl $C_{1-6}$ alkyl,
$C_{7-20}$ polycyclyl $C_{0-8}$ alkylsulfonylamino $C_{0-6}$ alkyl,
$C_{7-20}$ polycyclyl $C_{0-8}$ alkylcarbonylamino $C_{0-6}$ alkyl,
$C_{7-20}$ polycyclyl $C_{0-8}$ alkylaminosulfonyolamino $C_{0-6}$ alkyl,
$C_{7-20}$ polycyclyl $C_{0-8}$ alkylaminocarbonylamino $C_{0-6}$ alkyl, or
$C_{7-20}$ polycyclyl $C_{0-8}$ alkyloxycarbonylamino $C_{0-6}$ alkyl wherein any of the alkyl groups may be unsubstituted or substituted with $R^{11}$ and $R^{12}$, wherein any of the polycyclyl may be unsubstituted or substituted with $R^{18}$, $R^{19}$, $R^{20}$ and $R^{21}$, and provided that the carbon atom to which $R^8$ and $R^9$ are attached is itself attached to no more than one heteroatom; or $R^8$ and $R^9$ are combined to form oxo, in which case the carbon atom to which $R^8$ and $R^9$ are attached can itself be attached to more than one heteroatom;

$R^{10}$ is selected from
hydrogen,
$C_{1-8}$ alkyl,
aryl,
aryl $C_{1-8}$ alkyl,
aryl $C_{1-6}$ alkoxy,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, or
$C_{1-8}$ dialkylaminocarbonylmethylene;

m, n and r are each independently an integer from 0 to 3;
p is an integer from 1 to 4; and
q is an integer from 0 to 2;
and the pharmaceutically acceptable salts thereof.

In one embodiment of the invention is the compound wherein X is a 9- to 10-membered polycyclic ring system, wherein one or more of the rings is aromatic, and wherein the polycyclic ring system contains 0, 1, 2, 3 or 4 heteroatoms selected from N, O or S, and wherein the polycyclic ring system is either unsubstituted or substituted with $R^1$ and $R^2$; and
all other variables are as defined above;
and the pharmaceutically acceptable salts thereof.

In a class of the invention is the compound of the formula

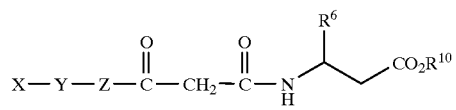

wherein X is selected from

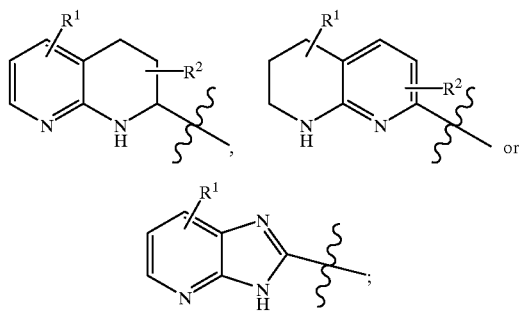

Z is absent or is selected from

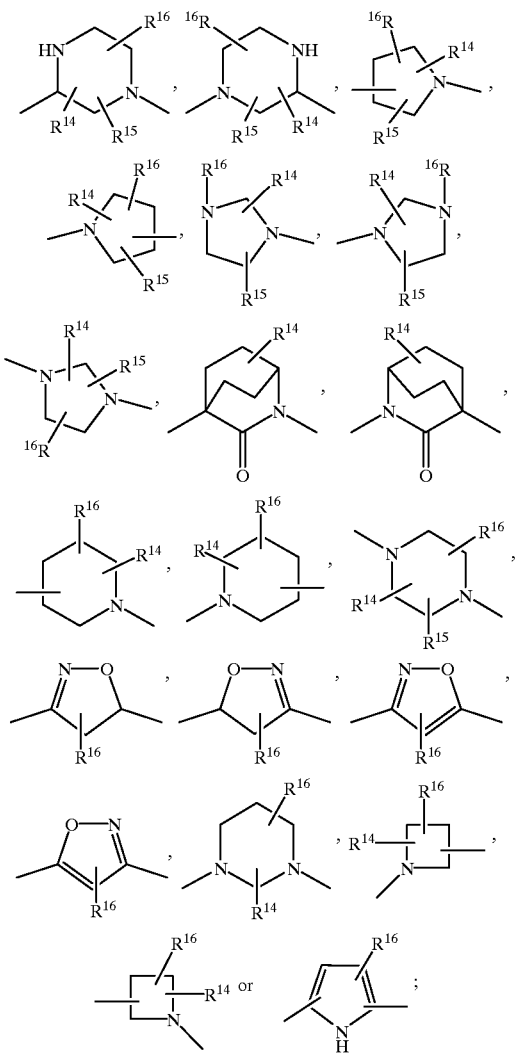

R⁶ is selected from
hydrogen,
aryl,
—(CH₂)$_p$-aryl,
C$_{1-8}$ alkyl, either unsubstituted or substituted, with one or more groups selected from: halogen, hydroxyl, C$_{1-5}$ alkylcarbonylamino, aryl C$_{1-5}$ alkoxy, C$_{1-5}$ alkoxycarbonyl, aminocarbonyl, C$_{1-5}$ alkylaminocarbonyl, C$_{1-5}$ alkylcarbonyloxy, C$_{3-8}$ cycloalkyl, oxo, amino, C$_{1-3}$ alkylamino, amino C$_{1-3}$ alkyl, arylaminocarbonyl, aryl C$_{1-5}$ alkylaminocarbonyl, aminocarbonyl, aminocarbonyl C$_{1-4}$ alkyl, hydroxycarbonyl, or hydroxycarbonyl C$_{1-5}$ alkyl,
HC≡C(CH₂)$_r$—
C$_{1-6}$ alkyl-C≡C(CH₂)$_r$—,
C$_{3-7}$ cycloalkyl-C≡C(CH₂)$_r$—,
aryl-C≡C(CH₂)$_r$—,
C$_{1-6}$ alkylaryl-C≡C(CH₂)$_r$—,
H₂C=CH(CH₂)$_r$—,
C$_{1-6}$ alkyl-CH=CH(CH₂)$_r$—,
C$_{3-7}$ cycloalkyl-CH=CH(CH₂)$_r$—,
aryl-CH=CH(CH₂)$_r$—,
C$_{1-6}$ alkylaryl-CH=CH(CH₂)$_r$—,
C$_{1-6}$ alkyl-SO₂(CH₂)$_r$—, or
C$_{1-6}$ alkylaryl-SO₂(CH₂)$_r$—;
and all other variables are as defined above;
and the pharmaceutically acceptable salts thereof.

In a subclass of the invention is a compound of the formula

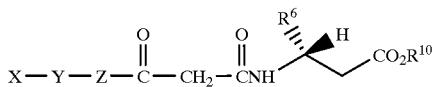

wherein Y is selected from

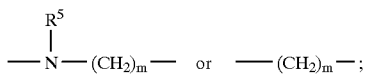

Z is absent or is selected from

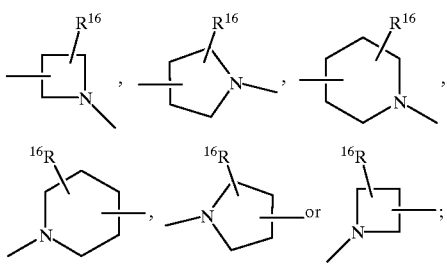

R⁶ is selected from
hydrogen,

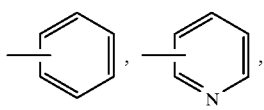

—(CH₂)p indolyl,
HC≡C(CH₂)$_r$—

C$_{1-6}$ alkyl-C≡C(CH₂)$_r$—,
C$_{3-7}$ cycloalkyl-C≡C(CH₂)$_r$—,
aryl-C≡C(CH₂)$_r$—,
C$_{1-6}$ alkylaryl-C≡C(CH₂)$_r$—,
H₂C=CH(CH₂)$_r$—,
C$_{1-6}$ alkyl-CH=CH(CH₂)$_r$—,
C$_{3-7}$ cycloalkyl-CH=CH(CH₂)$_r$—,
aryl-CH=CH(CH₂)$_r$—,
C$_{1-6}$ alkylaryl-CH=CH(CH₂)$_r$—,
C$_{1-6}$ alkyl-SO₂(CH₂)$_r$—, or
C$_{1-6}$ alkylaryl-SO₂(CH₂)$_r$—; and R¹⁰ is selected from hydrogen or C$_{1-8}$ alkyl; and all other variables are as defined above; and the pharmaceutically acceptable salts thereof Illustrative of the invention is the compound selected from Ethyl 3(S)-pyridin-3-yl-3-{2-[3-(5,6,7,8-tetrahydro-[1,8] naphthyridin-2-yl)propylcarbamoyl]acetylamino}propionate;

3(S)-pyridin-3-yl-3-{2-[3-(5,6,7,8-tetrahydro-[1,8] naphthyridin-2-yl)propylcarbamoyl]acetylamino}propionic acid;

3-(5,6,7,8-Tetrahydro-[1,8]naphthyridin-2-ylmethyl) piperidinyl-malonyl-3(S)-pyridin-3-yl-β-alanine ethyl ester;

3-(5,6,7,8-Tetrahydro-[1,8]naphthyridin-2-ylmethyl) piperidinyl-malonyl-3(S)-pyridin-3-yl-β-alanine;

4-(5,6,7,8-Tetrahydro-[1,8]naphthyridin-2-ylmethyl) piperidinyl-malonyl-3(S)-pyridin-3-yl-β-alanine ethyl ester;

4-(5,6,7,8-Tetrahydro-[1,8]naphthyridin-2-ylmethyl) piperidinyl-malonyl-3(S)-pyridin-3-yl-β-alanine;

4-(5,6,7,8-Tetrahydro-[1,8]naphthyridin-2-yl)piperidinyl-malonyl-3(S)-pyridin-3-yl-β-alanine ethyl ester; or 4-(5,6,7,8-Tetrahydro-[1,8]naphthyridin-2-yl)piperidinyl-malonyl-3(S)-pyridin-3-yl-β-alanine;

and the pharmaceutically acceptable salts thereof

Preferably, the compound is selected from

3(S)-Pyridin-3-yl-3-{2-[3-(5,6,7,8-tetrahydro-[1,8] naphthyridin-2-yl)propylcarbamoyl]acetylamino}propionic acid;

3-(5,6,7,8-Tetrahydro-[1,8]naphthyridin-2-ylmethyl) piperidinyl-malonyl-3(S)-pyridin-3-yl-β-alanine;

4-(5,6,7,8-Tetrahydro-[1,8]naphthyridin-2-ylmethyl) piperidinyl-malonyl-3(S)-pyridin-3-yl-β-alanine; or 4-(5,6,7,8-Tetrahydro-[1,8]naphthyridin-2-yl)piperidinyl-malonyl-3(S)-pyridin-3-yl-β-alanine;

and the pharmaceutically acceptable salts thereof

Exemplifying the invention is a pharmaceutical composition comprising any of the compounds described above and a pharmaceutically acceptable carrier. An example of the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Further illustrating the invention is a method of treating and/or preventing a condition mediated by antagonism of a vitronectin receptor in a mammal in need thereof, comprising administering to the mammal a therapeutically effective amount of any of the compounds described above. Preferably, the condition is selected from bone resorption, osteoporosis, restenosis, diabetic retinopathy, macular degeneration, angiogenesis, atherosclerosis, inflammation, cancer and tumor growth. More preferably, the condition is selected from osteoporosis and cancer. Most preferably, the condition is osteoporosis.

More specifically exemplifying the invention is a method of eliciting a vitronectin antagonizing effect in a mammal in need thereof, comprising administering to the mammal a therapeutically effective amount of any of the compounds or any of the pharmaceutical compositions described above. Preferably, the vitronectin antagonizing effect is an αvβ3 antagonizing effect; more specifically the αvβ3 antagonizing effect is selected from inhibition of bone resorption, inhibition of restenosis, inhibition of atherosclerosis, inhibition of angiogenesis, inhibition of diabetic retinopathy, inhibition of macular degeneration, inhibition of inflammation or inhibition of tumor growth. Most preferably, the αvβ3 antagonizing effect is inhibition of bone resorption. Alternatively, the vitronectin antagonizing effect is an αvβ5 antagonizing effect or a dual αvβ3/αvβ5 antagonizing effect. Examples of αvβ5 antagonizing effects are inhibition of: restenosis, atherosclerosis, angiogenesis, diabetic retinopathy, macular degeneration, inflammation or tumor growth. Examples of dual αvβ3/αvβ5 antagonizing effects are inhibition of: bone resorption, restenosis, atherosclerosis, angiogenesis, diabetic retinopathy, macular degeneration, inflammation or tumor growth.

Additional examples of the invention are methods of inhibiting bone resorption and of treating and/or preventing osteoporosis in a mammal in need thereof, comprising administering to the mammal a therapeutically effective amount of any of the compounds or any of the pharmaceutical compositions decribed above.

Further exemplifying the invention is any of the compounds or compositions described above, further comprising a therapeutically effective amount of a second bone resorption inhibitor; preferably, the second bone resorption inhibitor is alendronate.

More particularly illustrating the invention is any of the methods of treating and/or preventing osteoporosis and/or of inhibiting bone resoption described above, wherein the compound is administered in combination with a second bone resorption inhibitor; preferably, the second bone resorption inhibitor is alendronate.

Additional illustrations of the invention are methods of treating hypercalcemia of malignancy, osteopenia due to bone metastases, periodontal disease, hyperparathyroidism, periarticular erosions in rheumatoid arthritis, Paget's disease, immobilization-induced osteopenia, and glucocorticoid treatment in a mammal in need thereof, comprising administering to the mammal a therapeutically effective amount of any of the compounds or any of the pharmaceutical compositions described above.

More particularly exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone resorption, tumor growth, cancer, restenosis, artherosclerosis, diabetic retinopathy and/or angiogenesis.

Another illustration of the invention is a drug which is useful for treating and/or preventing osteoporosis in a mammal in need thereof, the effective ingredient of the said drug being any of the compounds descibed above. More specifically illustrating the invention is a drug which is useful for treating and/or preventing: bone resorption, tumor growth, cancer, restenosis, artherosclerosis, diabetic retinopathy and/or angiogenesis in a mammal in need thereof, the effective ingredient of the said drug being any of the compounds described above.

Additional illustrations of the invention are methods of treating tumor growth in a mammal in need thereof, comprising administering to the mammal a therapeutically effective amount of a compound described above and one or more agents known to be cytotoxic or antiproliferative, e.g., taxol and doxorubicin.

DETAILED DESCRIPTION OF THE INVENTION

Representative compounds of the present invention are avb3 antagonists which display submicromolar affinity for the human avb3 receptor. Compounds of this invention are therefore useful for treating mammals suffering from a bone condition caused or mediated by increased bone resorption, who are in need of such therapy. Pharmacologically effective amounts of the compounds, including pharmaceutically acceptable salts thereof, are administered to the mammal, to inhibit the activity of mammalian osteoclasts.

The compounds of the present invention are administered in dosages effective to antagonize the αvβ3 receptor where such treatment is needed, as, for example, in the prevention or treatment of osteoporosis. For use in medicine, the salts of the compounds of this invention refer to non-toxic "pharmaceutically acceptable salts." Other salts may, however, be useful in the preparation of the compounds according to the invention or of their pharmaceutically acceptable salts. Salts encompassed within the term "pharmaceutically acceptable salts" refer to non-toxic salts of the compounds of this invention which are generally prepared by reacting the free base with a suitable organic or inorganic acid. Representative salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The compounds of the present invention, may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention; further included are all mixtures of the two enantiomers. Also included within the scope of the invention are polymorphs and hydrates of the compounds of the instant invention.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "design of prodrugs," ed. H. Bundgaard, Elsevier, 1985. Metabolites of these compounds include active species produced upon introduction of compounds of this invention into the biological milieu.

The term "therapeutically effective amount" shall mean that amount of a drug or pharmaceutical agent that will elicit the biological or medical response of a tissue, system, animal or human that is being sought by a researcher or clinician.

The term "bone resorption," as used herein, refers to the process by which osteoclasts degrade bone.

The term "alkyl" shall mean straight or branched chain alkanes of one to ten total carbon atoms, or any number within this range (i.e., methyl, ethyl, 1-propyl, 2-propyl, n-butyl, s-butyl, t-butyl, etc.).

The term "alkenyl" shall mean straight or branched chain alkenes of two to ten total carbon atoms, or any number within this range.

The term "alkynyl" shall mean straight or branched chain alkynes of two to ten total carbon atoms, or any number within this range.

The term "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

The term "alkoxy," as used herein, refers to straight or branched chain alkoxides of the number of carbon atoms specified (e.g., $C_{1-5}$ alkoxy), or any number within this range (i.e., methoxy, ethoxy, etc.).

The term "aryl," as used herein, refers to a monocyclic or polycyclic system composed of 5- and 6-membered fully unsaturated or partially unsaturated rings, such that the system comprises at least one fully unsaturated ring, wherein the rings contain 0, 1, 2, 3 or 4 heteroatoms chosen from N, O or S, and either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino $C_{1-8}$ alkyl, $C_{1-6}$ dialkylamino, $C_{1-6}$ dialkylamino-$C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Examples of aryl include, but are not limited to, phenyl, naphthyl, pyridyl, pyrazinyl, pyrimidinyl, imidazolyl, benzimidazolyl, indolyl, thienyl, furyl, dihydrobenzofuryl, benzo(1,3) dioxolane, oxazolyl, isoxazolyl and thiazolyl, which are either unsubstituted or substituted with one or more groups independently selected from hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-5}$ alkoxycarbonyl, $C_{1-3}$ alkoxycarbonyl $C_{1-6}$ alkyl, hydroxycarbonyl $C_{1-6}$ alkyloxy, hydroxy, hydroxy $C_{1-6}$ alkyl, cyano, trifluoromethyl, oxo or $C_{1-5}$ alkylcarbonyloxy. Preferably, the aryl group is unsubstituted, mono-, di-, tri- or tetra-substituted with one to four of the above-named substituents; more preferably, the aryl group is unsubstituted, mono-, di- or tri-substituted with one to three of the above-named substituents; most preferably, the aryl group is unsubstituted, mono- or di-substituted with one to two of the above-named substituents.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The terms "arylalkyl" and "alkylaryl" include an alkyl portion where alkyl is as defined above and to include an aryl portion where aryl is as defined above. The $C_{0-m}$ or $C_{1-m}$ designation where m may be an integer from 1–10 or 2–10 respectively refers to the alkyl component of the arylalkyl or alkylaryl unit. Examples of arylalkyl include, but are not limited to, benzyl, fluorobenzyl, chlorobenzyl, phenylethyl, phenylpropyl, fluorophenylethyl, chlorophenylethyl, thienylmethyl, thienylethyl, and thienylpropyl. Examples of alkylaryl include, but are not limited to, toluene, ethylbenzene, propylbenzene, methylpyridine, ethylpyridine, propylpyridine and butylpyridine.

When any substituent includes the definition $C_0$ (e.g., aryl $C_{0-8}$ alkyl), the group modified by $C_0$ is not present in the substituent. Similarly, when any of the variables m, n, q or r is zero, then the group modified by the variable is not present; for example, when r is zero, the group "—$(CH_2)_r$—C≡CH" is "—C≡CH".

The term "halogen" shall include iodine, bromine, chlorine and fluorine.

The term "oxy" means an oxygen (O) atom. The term "thio" means a sulfur (S) atom. The term "oxo" shall mean=O.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally.

Under standard nonmenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to

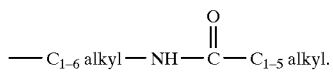

The present invention is also directed to combinations of the compounds of the present invention with one or more agents useful in the prevention or treatment of osteoporosis. For example, the compounds of the instant invention may be effectively administered in combination with effective amounts of other agents used in the treatment of osteoporosis such as bisphosphonate bone resorption inhibitors; preferably, the bone resorption inhibitor is the bisphosphonate alendronate, now sold as FOSAMAX®. Preferred combinations are simultaneous or alternating treatments of an αvβ3 receptor antagonist of the present invention and FOSAMAX®. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating αvβ3 related conditions includes in principle any combination with any pharmaceutical composition useful for treating osteoporosis.

As used herein, the term "composition" is intended to encompass a product comprising the specified ingredients in the specified amounts, as well as any product which results, directly or indirectly, from combination of the specified ingredients in the specified amounts.

The compounds of the present invention can be administered in such oral dosage forms as tablets, capsules (each of which includes sustained release or timed release formulations), pills, powders, granules, elixers, tinctures, suspensions, syrups and emulsions. Likewise, they may also be administered in intravenous (bolus or infusion), intraperitoneal, topical (e.g., ocular eyedrop), subcutaneous, intramuscular or transdermal (e.g., patch) form, all using forms well known to those of ordinary skill in the pharmaceutical arts. An effective but non-toxic amount of the compound desired can be employed as an αvβ3 inhibitor.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients or carriers (collectively referred to herein as 'carrier' materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In the schemes and examples below, various reagent symbols and abbreviations have the following meanings:

| | |
|---|---|
| AcOH: | Acetic acid. |
| $BH_3 \cdot DMS$: | Borane.dimethylsulfide. |
| BOC(Boc): | t-Butyloxycarbonyl. |
| BOP: | Benzotriazol-1-yloxytris(dimethylamino)-phosphonium hexafluorophosphate. |
| CBZ(Cbz): | Carbobenzyloxy or benzyloxycarbonyl. |
| CDI: | Carbonyldiimidazole. |
| $CH_2Cl_2$: | Methylene chloride. |
| $CHCl_3$: | Chloroform. |
| DEAD: | Diethyl azodicarboxylate. |
| DIAD: | Diisopropyl azodicarboxylate. |
| DIBAH or DIBAL-H: | Diisobutylaluminum hydride. |
| DIPEA: | Diisopropylethylamine. |
| DMAP: | 4-Dimethylaminopyridine. |
| DME: | 1,2-Dimethoxyethane. |

| | |
|---|---|
| DMF: | Dimethylformamide. |
| DMSO: | Dimethylsulfoxide. |
| DPFN: | 3,5-Dimethyl-1-pyrazolylformamidine nitrate. |
| DPPA: | Diphenylphosphoryl azide. |
| EDC: | 1-(3-Dimethylaminopropyl)-3-ethylcarbodiimide. |
| Et: | Ethyl. |
| EtOAc: | Ethyl acetate. |
| EtOH: | Ethanol. |
| HOAc: | Acetic acid. |
| HOBT: | 1-Hydroxybenzotriazole. |
| LDA: | Lithium diisopropylamide. |
| MeOH: | Methanol. |
| $NEt_3$: | Triethylamine. |
| NMM: | N-methylmorpholine. |
| PCA.HCl: | Pyrazole carboxamidine hydrochloride. |
| Pd/C: | Palladium on activated carbon catalyst. |
| Ph: | Phenyl. |
| pTSA | p-Toluene sulfonic acid. |
| TEA: | Triethylamine. |
| TFA: | Trifluoroacetic acid. |
| THF: | Tetrahydrofuran. |
| TLC: | Thin Layer Chromatography. |
| TMEDA: | N,N,N',N'-Tetramethylethylenediamine. |
| TMS: | Trimethylsilyl. |

The novel compounds of the present invention were prepared according to the procedure of the following schemes and examples, using appropriate materials and are further exemplified by the following specific examples. The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

The following Schemes and Examples describe procedures for making representative compounds of the present invention. Moreover, by utilizing the procedures described in detail in PCT International Application Publication Nos. WO95/32710, published Dec. 7, 1995, and WO95/17397, published Jun. 29, 1995, in conjunction with the disclosure contained herein, one of ordinary skill in the art can readily prepare additional compounds of the present invention claimed herein.

More specifically, procedures for preparing the N-terminus of the compounds of the present invention are described in WO 95/32710. Additionally, for a general review describing the synthesis of β-alanines which can be utilized as the C-terminus of the compounds of the present invention, see Cole, D. C., *Recent Stereoselective Synthetic Approaches to b-Amino Acids, Tetrahedron*, 1994, 50, 9517–9582; Juaristi, E, et al., *Enantioselective Synthesis of β-Amino Acids, Aldrichemica Acta*, 1994, 27, 3. In particular, synthesis of the 3-methyl β-alanine is taught in Duggan, M. F. et al., *J. Med. Chem.*, 1995, 38, 3332–3341; the 3-ethynyl β-alanine is taught in Zablocki, J. A., et al., *J. Med. Chem.*, 1995, 38, 2378–2394; the 3-pyrid-3-yl β-alanine is taught in Rico, J. G. et al., *J. Org. Chem.*, 1993, 58, 7948–7951; and the 2-amino and 2-toslylamino β-alanines are taught in Xue, C-B, et al., *Biorg. Med. Chem. Letts.*, 1996, 6, 339–344.

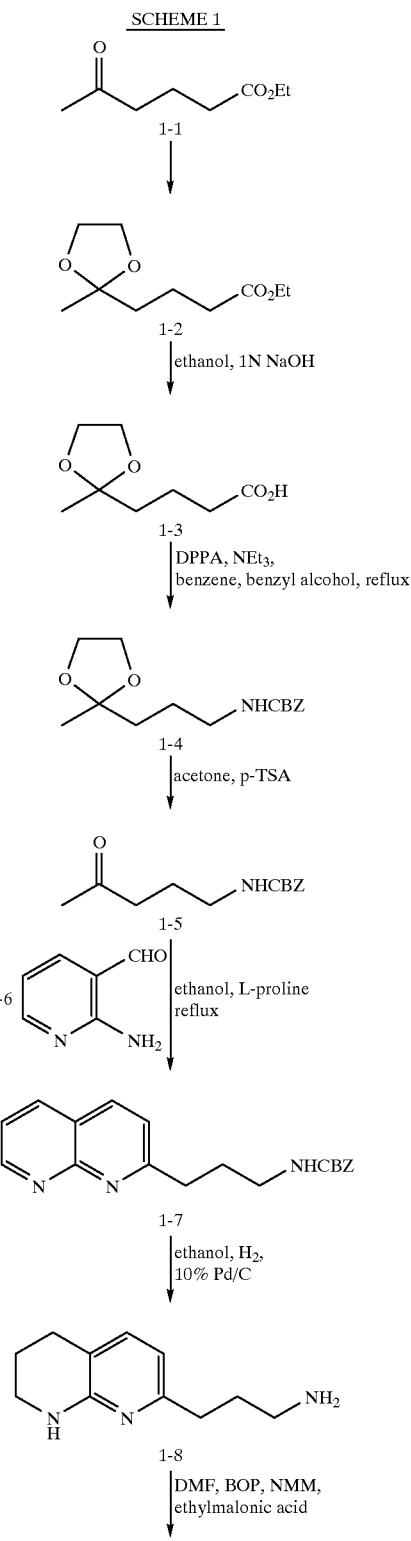

SCHEME 1

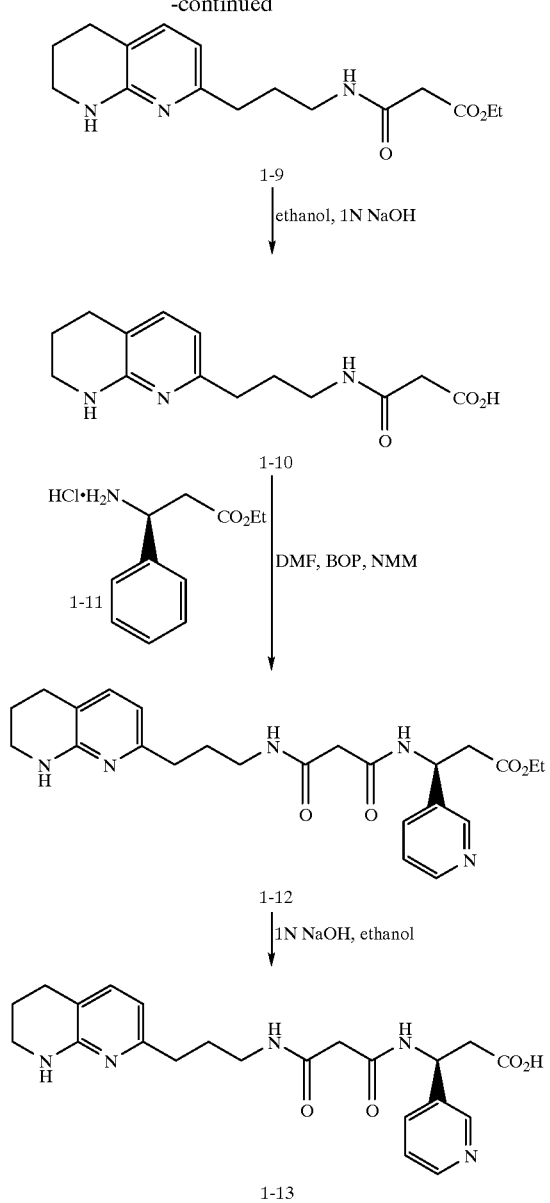

Ethyl 2-(ethylenedioxy)-pentanoate(1-2)

A solution of 1-1 (40.0 g, 250 mmol; Aldrich), ethylene glycol (17.2 g, 275 mmol), PTSA (10 mg), and benzene (400 mL) was refluxed for 20 h in a flask equipped with a Dean-Stark trap. The cooled reaction mixture was concentrated to give 1-2 as a yellow oil. TLC Rf=0.32 (EtOAc).

$^1$H NMR (300 MHz, CDCl$_3$) δ4.13 (q, J=7 Hz, 2H), 3.94 (m, 4H), 2.32 (m, 2H), 1.70 (m, 4H), 1.32 (s, 3H), 1.24 (t, J=7 Hz, 3H).

2-Ethylenedioxy-pentanoic acid (1-3)

A solution of 1-2 (2.0 g, 9.9 mmol), 1N NaOH (24.7 mL, 24.7 mmol), and ethanol (49 mL) was stirred at ambient temperature for 6 h followed by concentration. The residue was diluted with H$_2$O and EtOAc and then acidified with 10% KHSO$_4$. The organic phase was then washed with brine, dried (MgSO$_4$), and concentrated to give 1-3 as a colorless oil.

$^1$H NMR (300 MHz, CDCl$_3$) δ3.94 (m, 4H), 2.40 (m, 2H), 1.72 (m, 4H), 1.33 (s, 3H).

2-Ethylenedioxy-5-benzyloxycarbonylaminopentane (1-4)

A solution of 1-3 (1.66 g, 9.5 mmol), triethylamine (2.0 mL, 14.3 mmol), diphenylphosphorylazide (2.1 mL, 9.5 mmol), and benzene (48 mL) was heated at reflux for 2 h followed by addition of benzyl alcohol (1.5 mL, 14.3 mL). After 20 h, the cooled reaction mixture was diluted with EtOAc and washed with H$_2$O, 10% KHSO$_4$, Sat. NaHCO$_3$, and brine, dried (MgSO$_4$) and concentrated. Flash chromatography (silica, 35% EtOAc/hexanes) gave 1-4 as a colorless oil.

TLC Rf=0.41 (35% EtOAc/hexanes). $^1$H NMR (300 MHz, CDCl$_3$) δ7.36 (m, 5H), 5.09 (s, 2H), 4.89 (bs, 1H), 3.92 (m, 4H), 3.20 (m, 2H), 1.62 (m, 4H), 1.30 (s, 3H).

2-Oxo-5-Benzyloxycarbonylaminopentane (1-5)

A solution of 14 (1.4 g, 5.0 mmol), pTSA (47 mg, 0.25 mmol), and acetone (25 mL) was refluxed for 5 h. The cooled reaction mixture was treated with sat. NaHCO$_3$ (10 mL) and then concentrated. The residue was dissolved in EtOAc and washed with sat. NaHCO$_3$, H$_2$O, and brine, dried (MgSO$_4$), and concentrated to furnish 1-5 as a yellow oil.

TLC Rf=0.31 (silica, 30% EtOAc/hexanes). $^1$H NMR (300 MHz, CDCl$_3$) δ7.32 (m, 5H), 5.10 (s, 2H), 4.90 (bs, 1H), 3.20 (m, 2), 2.49 (m, 2), 2.13 (s, 3H), 1.69 (m, 2H).

1-Benzyloxycarbonylamino3-([1,8]naphthyridin-2-yl)-propane (1-7)

A mixture of 1-5 (0.6 g, 2.51 mmol), 1-6 (0.3 g, 2.5 nmol; for preparation see Het., 1993, 36, 2513) and L-proline (0.0.87 g, 0.75 mmol) in absolute ethanol (13 mL) was heated at reflux for 20 h. Following evaporative removal of the solvent, the residue was chromatographed on silica gel, eluting with 0–5% isopropanol/EtOAc to give 1-7 as a yellow oil.

TLCRf=0.20 (ethyl acetate). $^1$H NMR (300 MHz, CHCl$_3$) δ9.08 (m, 1H), 8.16 (m, 1H), 8.10 (d, J=8 Hz, 1H), 7.50–7.30 (m, 8H), 5.08 (m, 3H), 3.33 (m, 2H), 3.11 (m, 2H), 2.15 (m, 2H).

3-(5,6,7,8-Tetrahydro-[1,8]naphthyridin-2-yl) propylamine (1-8)

A mixture of 1-7 (0.40 g, 1.24 mmol) and 10% Pd/carbon (0.08 g) in EtOH (12 mL) was stirred under a balloon of hydrogen for 20 h. Filtration through a celite pad and then evaporative removal of the filtrate solvent gave 1-8 as a colorless oil.

TLC Rf=0.47 (silica, 10:1:1 ethanol/NH$_4$OH/H$_2$O).

$^1$H NMR (300 MHz, CD$_3$OD) δ7.12 (d, J=7 Hz, 1H), 6.48 (d, J=7 Hz, 1H), 3.37 (m, 2H), 2.75–2.50 (m, 6H), 1.70–1.90 (m, 4H),

Ethyl 2-[3-(5,6,7,8-tetrahydro-[1,8]naphthyridin-2-yl)-propylcarbamoyl]-acetate (1-9)

A mixture of 1-8 (0.068 g, 0.36 mmol), ethylmalonic acid (0.052 g, 0.40 mmol), BOP (0.24 g, 0.54 mmol), and NMM (0.16 mL, 1.4 mmol) in DMF (1.8 mL) was stirred at ambient temperature for 20 h. The mixture was diluted with ethyl acetate, washed with water, brine, and dried over MgSO$_4$. Following evaporative removal of the solvent, the residue was chromatographed on silica gel, eluting with 15% ethanol/EtOAc to give 1-9 as a colorless glass.

TLC Rf=0.26 (silica, 15% ethanol/EtOAc), $^1$H NMR (300 MHz, CD$_3$OD) δ7.12 (d, J=7 Hz, 1H), 6.47 (d, J=7 Hz, 1H), 4.17 (q, J=7 Hz, 2H), 3.37 (m, 2H), 3.20 (m, 4H), 2.70 (m, 2H), 2.54 (m, 2H), 1.86 (m, 4H), 1.24 (t, J=7 Hz, 3H).

2-[3-(5,6,7,8-Tetrahydro-[1,8]naphthyridin-2-yl)-propylcarbamoyl]-acetic acid (1-10)

To a solution of 1-9 (0.072 g, 0.24 mmol) in EtOH (1.2 mL) was added 1N NaOH (0.6 ml, 0.6 mmol). After stirring for 2 h, the reaction mixture was neutralized with 1N HCl (0.6 mL) and then concentrated to give 1-10 and NaCl.

TLC Rf=0.25 (silica, 3:1 [20:1:1 ethanol:NH$_4$OH:H$_2$O/EtOAc], $^1$H NMR (300 MHz, CD$_3$OD) δ7.53 (d, J=7 Hz, 1H), 6.60 (d, J=7 Hz, 1H), 3.48 (m, 2H), 3.20 (m, 4H), 2.79 (m, 4H), 1.92 (m, 4H).

Ethyl 3(S)-pyridin-3-yl -3-{2-[3-(5,6,7,8-tetrahydro-[1,8]naphthyridin-2-yl)-propylcarbamoyl]-acetylamino}propionate (1-12)

A mixture of 1-10 (0.072 g, 0.24 mmol), 1-11 (0.064 g, 0.24 mmol), BOP (0.16 g, 0.36 mmol), and NMM (0.13 mL, 1.2 mmol) in DMF (2 mL) was stirred at ambient temperature for 20 h. The mixture was diluted with ethyl acetate, washed with water, brine, and dried over MgSO$_4$. Following evaporative removal of the solvent, the residue was chromatographed on silica gel, eluting with 1:3 [20:1:1 ethanol:NH$_4$OH:H$_2$O/EtOAc to give 1-12 as a colorless glass.

TLC Rf=0.64 (silica, 1:3 [20:1:1 ethanol:NH$_4$OH:H$_2$O/EtOAc], $^1$H NMR (300 MHz, CHCl$_3$) δ8.61 (m, 1H), 8.51 (m, 1H), 8.29 (d, J=8 Hz, 1H), 7.85 (m, 1H), 7.65 (m, 1H), 7.23 (m, 1H), 7.05 (d, J=7 Hz, 1H), 6.32 (d, J=7 Hz, 1H), 5.47 (m, 1H), 5.23 (bs, 1H), 4.09 (q, J=7 Hz, 2H), 3.5–2.5 (m, 12H), 1.88 (m, 4H), 1.18 (t, J=7 Hz, 3H).

3(S)-Pyridin-3-yl -3-{2-[3-(5,6,7,8-tetrahydro-[1,8]naphthyridin-2-yl)propylcarbamoyl]-acetylamino}propionic acid bis(trifluoracetate) (1-13)

To a solution of 1-12 (0.050 g, 0.11 mmol) in EtOH (1 mL) was added 1N NaOH (0.27 ml, 0.27 mmol). After stirring for 2 h, the reaction mixture was neutralized with 1N HCl and the solvents evaporated. Prep HPLC (95:5 to 50:50 H$_2$O/CH$_3$CN(0.1% TFA) over 60 min gave 1-13 as a colorless oil.

$^1$H NMR (300 MHz, D$_2$O) δ8.85 (m, 1H), 8.72 (d, J=8 Hz, 1H), 8.64 (d, J=8 Hz, 1H), 8.08 (d, J=8 Hz, 1H), 8.05 (d, J=8 Hz, 1H), 7.05 (d, J=7 Hz, 1H), 6.55 (d, J=7 Hz, 1H), 5.48 (t, J=7 Hz, 1H), 3.45 (m, 2H), 3.22 (m, 2H), 3.08 (d, J=7Hz, 2H), 2.76 (m, 2H), 2.65 (m, 2H), 1.88 (m, 4H).

SCHEME 2

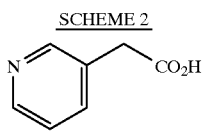

2-1 a) PtO$_2$, AcOH/H$_2$O, H$_2$
b) CH$_3$CN, BocO$_2$, 1N NaOH

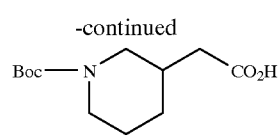

2-2 ether, MeLi, 0° C

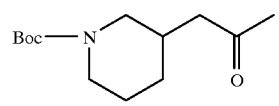

2-3

2-amino-3-carboxaldehydepyridine (1-6), ethanol, L-proline, reflux

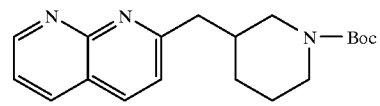

2-4

10% Pd/C, ethanol, H$_2$

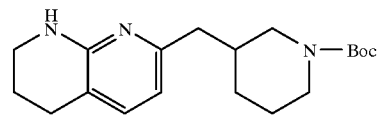

2-5

HCl/dioxane

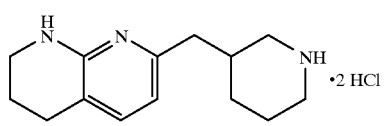

2-6 ethyl hydrogen malonate, EDC, HOBT, NMM, DMF

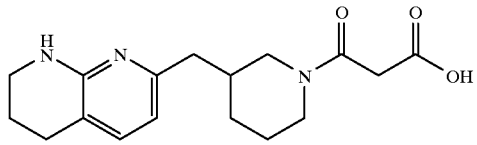

2-7 a) 1N NaOH, ethanol
b) EDC, HOBT, NMM, DMF

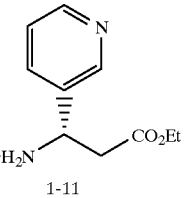

1-11

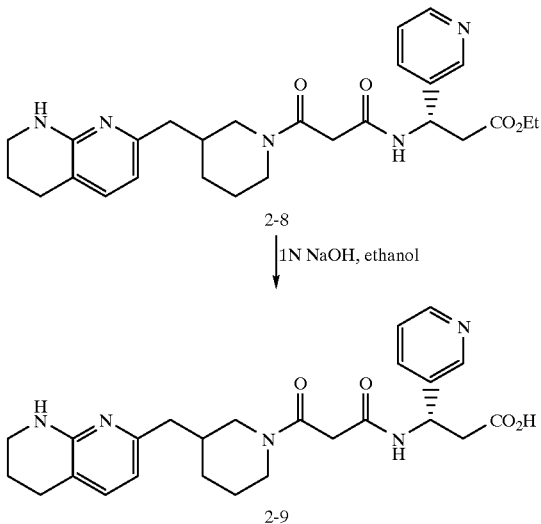

2-8

↓1N NaOH, ethanol 2-9

N-Boc-Piperidin-3-ylacetic acid (2-2)

A mixture of 2-1 (15 g, 87 mmol), AcOH (125 mL), $H_2O$ (25 mL), and $PtO_2$ (1.5 g) was shaken under a hydrogen atmosphere (55 PSI) on the Parr apparatus for 4 hr. The reaction mixture was filtered through a celite pad and the filtrate concentrated. The residue was suspended in acetonitrile (500 mL) and 1N NaOH was added until the solid dissolved and the mixture was basic. $Boc_2O$ (20.8 g, 95 mmol) was added and the reaction mixture stirred overnight. The acetonitrile was evaporated and the aqueous phase acidified with 10% $KHSO_4$. Extraction with EtOAc followed by washing the organic phase with brine, drying ($MgSO_4$), and concentration gave 2-2 as a clear oil.

$^1H$ NMR (300 MHz, $CDCl_3$) δ3.90 (m, 1H), 3.80 (m, 1H), 2.82 (m, 1H), 2.70 (m, 1H), 2.4–1.2 (m, 7H).

N-Boc-3-(propan-2-one)piperidine (2-3)

A solution of 2-2 (13.4 g, 55 mmol) and ether (500 mL) at 0° C. was treated dropwise with MeLi (87 mL, 121 mmol; 1.4 M/ether). After addition was complete the cooling bath was removed and the reaction mixture stirred overnight. The reaction mixture was then poured into a ice/water mixture and then extracted with ether. The ether extracts were washed with brine, dried($MgSO_4$), and concentrated. Flash chromatography (silica, 30% EtOAc/hexanes) gave 2-3 as a colorless oil.

TLC Rf=0.59 (silica, 30% EtOAc, hexanes), $^1H$ NMR (300 MHz, $CDCl_3$) δ3.80 (m, 2H), 2.92 (m, 1H), 2.64 (m, 1H), 2.40 (m, 1H), 2.28 (m, 1H), 2.15 (s, 3H), 2.03 (m, 1H), 1.80 (m, 1H), 1.63–1.00 (m, 1H), 1.45 (s, 9H).

N-Boc-3-([1,8]-Naphthyridin-2-ylmethyl)piperidine (2-4)

A mixture of 2-3 (74 mg, o.31 mmol), 2-3a (38 mg, 0.31 mmol), L-proline (18 mg, 0.15 mmol), and ethanol (4 mL) was refluxed for 20 hr. The cooled reaction mixture was concentrated and then purified by flash chromatography (silica, EtOAc) to give 24 as a yellow solid.

TLC Rf=0.24 (silica, EtOAc), $^1H$ NMR (300 MHz, $CDCl_3$) δ9.10 (m, 1H), 8.18 (dd, J=8 and 2 Hz, 1H), 8.11 (d, J=8 Hz, 1H), 7.46 (m, 1H), 7.38 (d, J=8 Hz, 1H), 3.90 (m, 2H), 3.05–2.60 (m, 3H), 2.22 (m, 1H), 1.81 (m, 1H), 1.68 (m, 2H), 1.40 (s, 9H), 1.30 (m, 2H).

N-Boc-3-(5,6,7,8-Tetrahydro-[1,8]naphthyridin-2-ylmethyl)-piperidine (2-5)

A mixture of 24 (1.1 g, 3.3 mmol), 10% Pd/C (108 mg), and ethanol (20 mL) was stirred under a hydrogen atmosphere (1 atm) for 20 hr. The reaction mixture was then filtered through a celite pad and the filtrate concentrated. Flash chromatography (silica, 80% hexanes/EtOAc) gave 2-5 as a colorless oil.

TLC Rf=0.21 (silica, EtOAc), $^1H$ NMR (300 MHz, $CDCl_3$) δ7.03 (d, J=8 Hz, 1H), 6.32 (d, J=8 Hz, 1H), 4.79 (bs, 1H), 3.90 (m, 2H), 3.40 (m, 2H), 2.78 (m, 1H), 2.70 (m, 2H), 2.57 (m, 1H), 2.44 (m, 2H), 1.90–1.00 (m, 7H), 1.41 (s, 9H).

3-(5,6,7,8-Tetrahydro-[1,8]naphthyridin-2-ylmethyl) piperidine .2 HCl (2-6)

HCl gas was bubbled through a solution of 2-5 (0.8 g, 2.5 mmol) and EtOAc (15 mL) at 0° C. for 15 min. After an additional 15 min argon was passed through the solution for 15 min followed by concentration. The residue was azeotroped twice with ether to give 2-6 as a yellow solid.

$^1H$ NMR (300 MHz, $CD_3OD$) δ7.60 (d, J=8 Hz, 1H), 6.63 (d, J=8 Hz, 1H), 3.52 (m, 2H), 3.36 (m, 2H), 3.00–2,60 (m, 6H), 2.24 (m, 1H), 2.00–1.70 (m, 4H), 1.35 (m, 2H).

Ethyl 3-(5,6,7,8-tetrahydro-[1,8]naphthyridin-2-ylmethyl)piperidinyl-malonate (2-7)

A mixture of 2-6 (200 mg, 0.66 mmol), ethyl hydrogen malonate (80 mg, 0.60 mmol), HOBT (97 mg, 0.80 mmol), NMM (0.53 mL, 5.3 mmol), and DMF (4 mL) was treated with EDC (138 mg, 0.80 mmol). After 20 hr, the reaction mixture was diluted with EtOAc and then washed with sat. $NaHCO_3$, $H_2O$, and brine, dried ($MgSO_4$), and concentrated. Flash chromatography (silica, 20% methanol/EtOAc) gave impure 2-7 as an oil which was used directly in the next step.

TLC Rf=0.62 (silica, 20% methanol/EtOAC)

3-(5,6,7,8-Tetrahydro-[1,8]naphthyridin-2-ylmethyl) piperidinyl-malonyl-3(S)-pyridin-3-yl-β-alanine ethyl ester (2-8)

A solution of 2-7 (200 mg, 0.6 mmol), 1N NaOH (0.6 mL), and ethanol (3 mL) was stirred at ambient temperature for 1 hr. The reaction mixture was then treated with 1N HCl (0.6 mL) and concentrated to give a semi-solid. The residue was dissolved in DMF (2 mL) and treated sequentially with 1–11 (150 mg, 0.56 mmol), HOBT (65 mg, 0.48 mmol), NMM (265 uL, 2.4 mmol), and EDC (92 mg, 0.48 mmol). After 72 hr, the reaction mixture was diluted with EtOAc and then washed with sat, $NaHCO_3$, $H_2O$, and brine, dried ($MgSO_4$), and concentrated. Flash chromatography (silica, 20% methanol/EtOAc) gave 2-8 as a yellowish oil.

TLC Rf=0.13 (silica, 20% methanol/EtOAc), $^1H$ NMR (300 MHz, $CDCl_3$) δ9.29 (bt, 1H), 8.60 (m, 1H), 8.50 (m, 1H), 7.70 (m, 1H), 7.23 (m, 1H), 7.03 (m, 1H), 6.38 (m, 1H), 5.49 (m, 1H), 4.10 (q, J=7 Hz, 2H), 3.73 (2H), 3.40 (m, 4H), 3.20–2.40 (m, 8H), 2.00–1.20 (m, 7H), 1.17 (t, J=7 Hz, 3H)

3-(5,6,7,8-Tetrahydro-[1,8]naphthyridin-2-ylmethyl) piperidinyl-malonyl-3(S)-pyridin-3-yl-β-alanine (2-9)

A mixture of 2-8 (20 mg, 40 umol), 1N NaOH (60 uL), and ethanol (2 mL) was stirred at ambient temperature for 3 hr. The reaction mixture was treated with 1N HCl (60 uL) and then concentrated. Flash chromatography (silica, 25:10:1:1 to 12:10:1:1 EtOAc/ethanol/H$_2$O/NH$_4$OH) gave 2-9 as a white solid.

TLC Rf=0.31 (silica, 50% EtOAc/[10:1:1 ethano/H$_2$O/NH$_4$OH]), $^1$H NMR (300 MHz, D$_2$O) δ8.55 (m, 1H), 8.44 (m, 1H), 7.93 (m, 1H), 7.52 (m, 2H), 6.50 (m, 1H), 5.25 (m, 1H), 3.80–3.40 (m, 8H), 3.00–2.40 (m, 8 H), 2.00–1.20 (m, 6H).

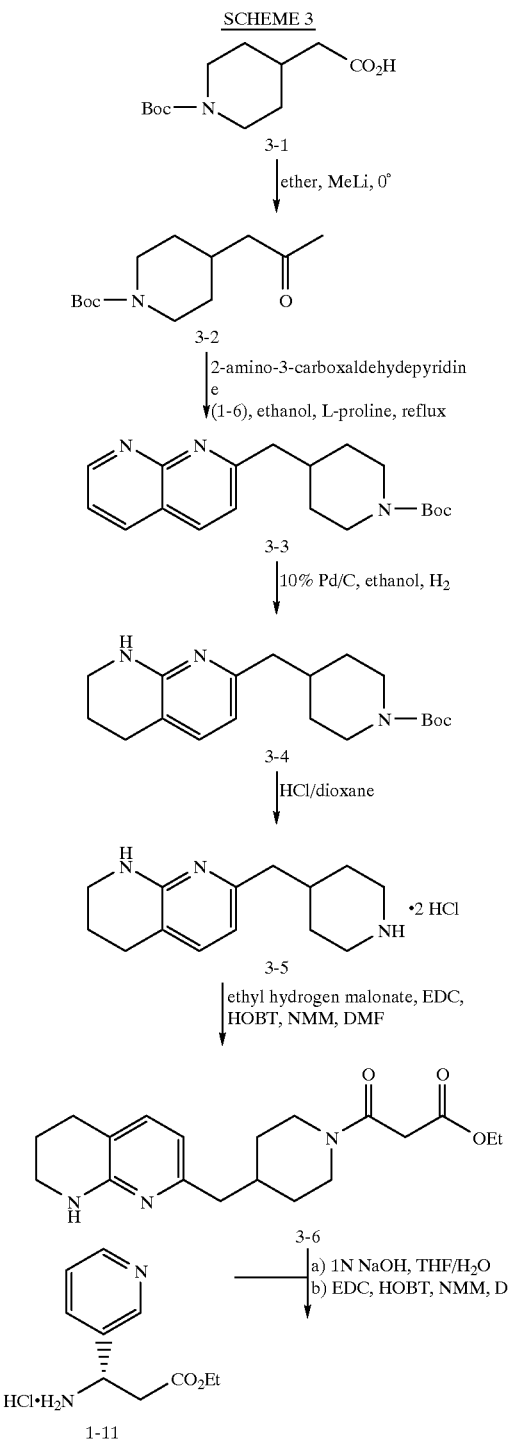

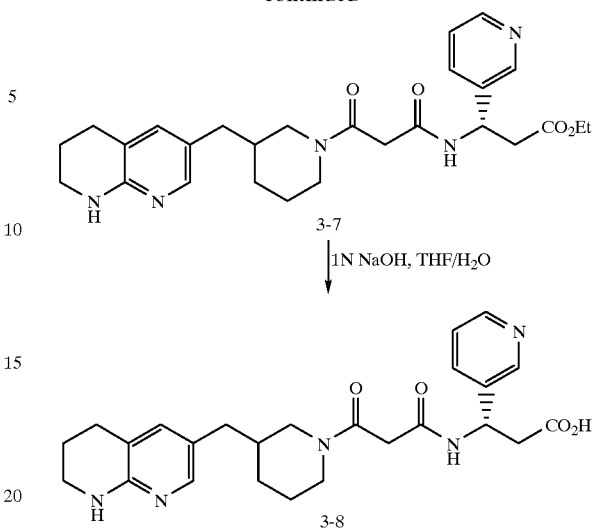

N-Boc-4-(propan-2-one)piperidine (3-2)

A solution of 3-1 (10 g, 41 mmol) and ether (400 mL) at 0° C. was treated dropwise with MeLi (66 mL, 92 mmol; 1.4 M/ether). After addition was complete the cooling bath was removed and the reaction mixture stirred overnight. The reaction mixture was then poured into a ice/water mixture and then extracted with ether. The ether extracts were washed with brine, dried(MgSO$_4$), and concentrated to give 3-2 as an oil.

1H NMR (300 MHz, CDCl$_3$) δ4.08 (m, 2H), 2.72 (bt, J=12 Hz, 2H), 2.36 (d, J=7 Hz, 2H), 2.14 (s, 3H), 1.97 (m, 1H), 1.63 (m, 2H), 1.45 (s, 9H), 1.10 (m, 2H).

N-Boc-4-([1,8]-Naphthyridin-2-ylmethyl)piperidine (3-3)

A mixture of 3-2 (2.5 g, 10.4 mmol), 1-6 (1.3 g, 10.4 mmol), L-proline (0.6 g, 5.2 mmol), and ethanol (70 mL) was refluxed for 20 hr. The cooled reaction mixture was concentrated and then purified by flash chromatography (silica, EtOAc) to give 3-3 as a yellow solid.

TLC Rf=0.28 (silica, EtOAc), $^1$H NMR (300 MHz, CDCl$_3$) δ9.10 (m, 1H), 8.18 (dd, J=8 and 2 Hz, 1H), 8.11 (d, J=8 Hz, 1H), 7.46 (m, 1H), 7.35 (d, J=8 Hz, 1H), 4.08 (m, 2H), 2.97 (d, J=8 Hz, 2H), 2.70 (m, 2H), 2.24 (m, 1H), 1.68 (m, 2H), 1.45 (s, 9H), 1.27 (m, 2H).

N-Boc-4-(5,6,7,8-Tetrahydro-[1,8]naphthyridin-2-ylmethyl)-piperidine (3-4)

A mixture of 3-3 (2.1 g, 6.4 mmol), 10% Pd/C (210 mg), and ethanol (32 mL) was stirred under a hydrogen atmosphere (1 atm) for 20 hr. The reaction mixture was then filtered through a celite pad and the filtrate concentrated. Flash chromatography (silica, 70% hexanes/EtOAc to EtOAc) gave 34 as a colorless oil.

TLC Rf=0.15 (silica, EtOAc), $^1$H NMR (300 MHz, CDCl$_3$) δ7.03 (d, J=8 Hz, 1H), 6.30 (d, J=8 Hz, 1H), 4.75 (bs, 1H), 4.08 (m, 2H), 3.40 (m, 2H), 2.69 (m, 3H), 2.44 (d, J=8 Hz, 2H), 1.90–1.00 (m, 8H), 1.43 (s, 9H).

4-(5,6,7,8-Tetrahydro-[1,8]naphthyridin-2-ylmethyl) piperidine .2 HCl (3-5)

A solution of 3-4 (1.6 g, 4.8 mmol) and dioxane (24 mL) at 0oC was treated with 4M HCl/dioxane (6.0 mL) followed by removal of the cooling bath. After 5 hr the reaction mixture was concentrated to give 3-5 as a yellow solid.

$^1$H NMR (300 MHz, CD$_3$OD) δ7.60 (d, J=8 Hz, 1H), 6.63 (d, J=8 Hz, 1H), 3.52 (m, 2H), 3.40 (m, 2H), 3.0 (bt, 2H), 2.83 (m, 2H), 2.71 (d, J=8 Hz, 2), 2.08 (m, 1H), 2.00–1.85 (m, 4H), 1.50 (m, 2H).

Ethyl 4-(5,6,7,8-tetrahydro-[1,8]naphthyridin-2-ylmethyl)piperidinyl-malonate (3-6)

A mixture of 3-5 (150 mg, 0.52 mmol), ethyl hydrogen malonate (76 mg, 0.57 mmol), HOBT (70 mg, 0.52 mmol), NMM (0.29 mL, 2.1 mmol), and DMF (4 mL) was treated with EDC (97 mg, 0.52 mmol). After 20 hr, the reaction mixture was diluted with EtOAc and then washed with sat. NaHCO$_3$, H$_2$O, and brine, dried (MgSO$_4$), and concentrated. Flash chromatography (silica, 15% methanol/EtOAc) gave impure 3-6 as an oil.

$^1$H NMR (300 MHz, CDCl$_3$) δ7.05 (d, J=8 Hz, 1H), 6.28 (d, J=8 Hz, 1H), 4.80 (bs, 1H), 4.58 (m, 1H), 4.20 (q, J=7 Hz, 2H), 3.70 m, 1H), 3.42 (m, 4H), 3.03 (m, 1H), 2.70 (m, 2H), 2.57 (m, 1H), 2.45 (d, J=7 Hz, 2H), 2.00–1.00 (m, 7H), 1.28 (t, J=7 Hz, 3H).

4-(5,6,7,8-Tetrahydro-[1,8]naphthyridin-2-ylmethyl) piperidinyl-malonyl-3(S)-pyridin-3-yl-β-alanine ethyl ester (3-7)

A solution of 3-6 (28 mg, 0.08 mmol), 1N NaOH (0.2 mL), THF (1 mL), and H$_2$O (1 mL) was stirred at ambient temperature for 1 hr. The reaction mixture was then treated with 1N HCl (0.2 mL) and concentrated to give a semi-solid. The residue was dissolved in DMF (3 mL) and treated sequentially with 1-11 (24 mg, 0.088 mmol), HOBT (12 mg, 0.088 mmol), NMM (87 uL, 0.63 mmol), and EDC (17 mg, 0.088 mmol). After 20 hr, the reaction mixture was diluted with EtOAc and then washed with sat, NaHCO$_3$, H$_2$O, and brine, dried (MgSO$_4$), and concentrated. Flash chromatography (silica, 70:25:5 CHCl$_3$/methanol/EtOAc) gave 3-7 as a yellowish oil.

$^1$H NMR (300 MHz, CDCl3) δ8.97 (d, J=8 Hz, 0.5H), 8.85 (d, J=8 Hz, 0.5H), 8.60 (m, 1H), 8.50 (m, 1H), 7.68 (m, 1H), 7.23 (m, 1H), 7.07 (d, J=8 Hz, 1H), 6.28 (m, 1H), 5.49 (m, 1H), 5.18 (m, 1H), 4.60 (d, J=13 Hz, 1H), 3.84 (d, J=13 Hz, 1H), 4.10 (q, J=7 Hz, 2H), 3.73 (2H), 3.40 (m, 2H), 3.10–2.80 (m, 4H), 2.70 (m, 1H), 2.67 (m, 1H), 2.45 (m, 1H), 1.95 (m, 4H), 1.70 (m, 3H), 1.17 (m, 2H), 1.17 (t, J=7 Hz, 3H)

4-(5,6,7,8-Tetrahydro-[1,8]naphthyridin-2-ylmethyl) piperidinyl-malonyl-3(S)-pyridin-3-yl-β-alanine (3-8)

A mixture of 3-7 (8.8 mg, 18 umol), 1N NaOH (44 uL), THF (0.2 mL), and H$_2$O (0.2 mL) was stirred at ambient temperature for 3 hr. The reaction mixture was treated with 1N HCl (66 uL) and then concentrated. Flash Chromatography (silica, 15:10:1:1 to 12:10:1:1 EtOAc/ethanol/H$_2$O/NH$_4$OH) gave 3-8 as a white solid.

TLC Rf=0.15 (silica, 15:10:1:1 EtOAc/ethanol/H$_2$O/NH$_4$OH), $^1$H NMR (300 MHz, CD$_3$OD) δ8.58 (m, 1H), 8.42 (m, 1H), 7.86 (m, 1H), 7.42 (m, 2H), 6.50 (m, 1H), 5.40 (m, 1H), 4.48 (m, 1H), 3.88 (m, 1H), 3.70–3.00 (m, 5H), 3.00–2.40 (m, 7 H), 2.00–1.00 (m, 7H).

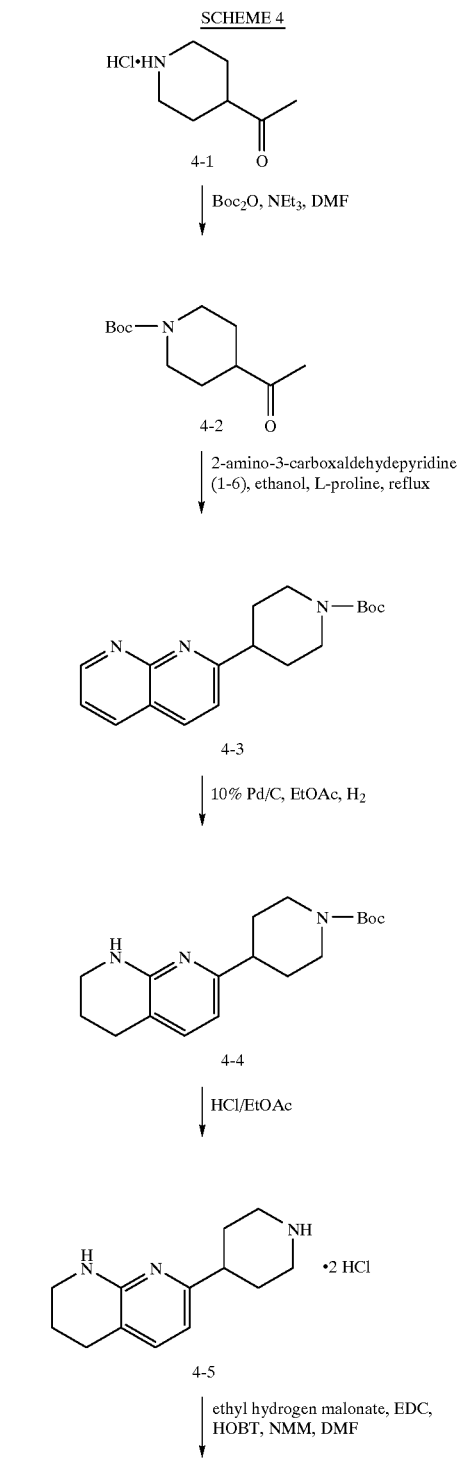

SCHEME 4

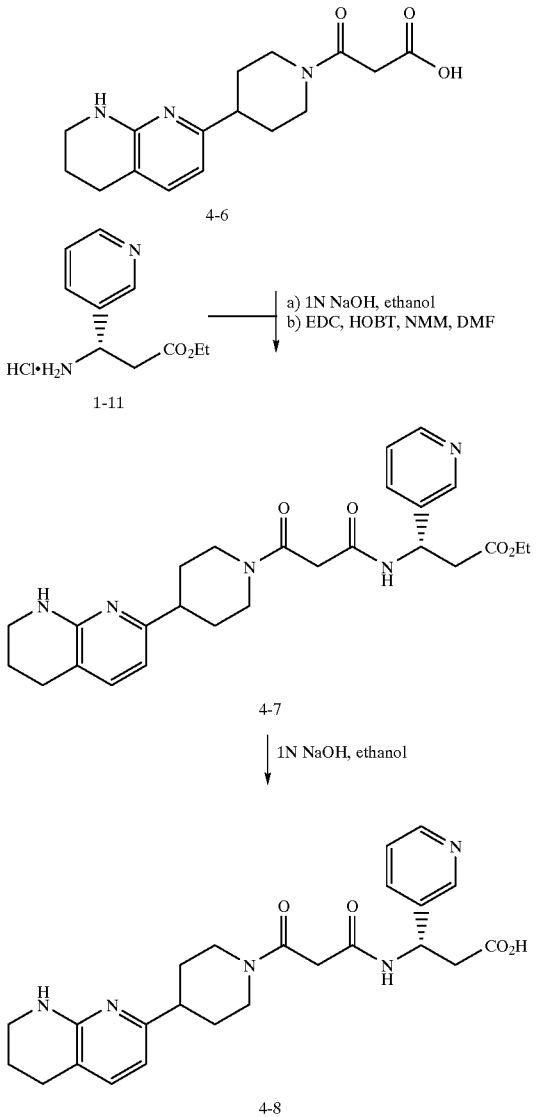

N-Boc-4-Acetylpiperidine (4-2)

To a stirred suspension of 4-1 (5.2 g, 32 mmol), NEt₃ (5.3 mL, 38 mmol), and DMF (100 mL) at 0°C was added Boc₂O followed by removal of the cooling bath. After 20 hr, the reaction mixture was diluted with EtOAc and then washed with H₂O, sat. NaHCO₃, 5% KHSO₄, and brine, dried(MgSO₄), and concentrated. Flash chromatography (silica, 30% EtOAc/hexanes) gave 4-2 as a colorless oil.

TLC Rf=0.31 (silica, 30% EtOAc/hexanes), ¹H NMR (300 MHz, CDCl₃) δ4.08 (bs, 2H), 2.80 (m, 2H), 2.45 (m, 1H), 2.17 (s, 3H), 1.83 (m, 2H), 1.48 (m, 2H), 1.46 (s, 9H).

N-Boc-4-([1.8]-Naphthyridin-2-yl)piperidine (4-3)

A mixture of 4-2 (4.0 g, 17,6 mmol), 1-6 (2.1 g, 17.6 mmol), L-proline (0.3 g, 2.6 mmol), and ethanol (88 mL) was refluxed for 40 hr. The cooled reaction mixture was concentrated and then purified by flash chromatography (silica, 30% EtOAc/hexanes to 3% isopropanol/EtOAc) to give 4-3 as a yellow solid.

TLC Rf=0.29 (silica, EtOAc), ¹H NMR (300 MHz, CDCl₃) δ9.10 (m, 1H), 8.18 (m 1H), 8.11 (d, J=8 Hz, 1H), 7.46 (m, 1H), 7.41 (d, J=8 Hz, 1H), 4.30 (m, 2H), 3.14 (m, 1H), 2.90 (m, 2H), 2.00 (m, 4H), 1.45 (s, 9H).

N-Boc-4-(5,6,7,8-Tetrahydro-[1,8]naphthyridin-2-yl) piperidine (4-4)

A mixture of 4-3 (2.6 g, 8.4 mmol), 10% Pd/C (0.52 g), and EtOAc (100 mL) was stirred under a hydrogen atmosphere (1 atm) for 20 hr. The reaction mixture was then filtered through a celite pad and the filtrate concentrated. Flash chromatography (silica, 70% hexanes/EtOAc to EtOAc) gave 4-4 as a colorless oil.

TLC Rf=0.15 (silica, 10% isopropanol/EtOAc), ¹H NMR (300 MHz, CDCl₃) δ7.13 (d, J=8 Hz, 1H), 6.33 (d, J=8 Hz, 1H), 4.20 (m, 2H), 3.42 (m, 2H), 2.79 (m, 2H), 2.70 (m, 2H), 2.62 (m, 1H), 1.90 (m, 4H), 1.60 (m, 2H), 1.43 (s, 9H).

4-(5,6,7,8-Tetrahydro-[1,8]naphthyridin-2-yl) piperidine.2 HCl (4-5)

HCl gas was bubbled through a solution of 4-4 (1.6 g, 4.8 mmol) and EtOAc (40 mL) at 0° C. for 3 min. The solution was stirred for an additional 1 hr followed by concentration to give 4-5 as a yellow foam.

¹H NMR (300 MHz, CD₃OD) δ7.63 (d, J=8 Hz, 1H), 6.67 (d, J=8 Hz, 1H), 3.52 (m, 4H), 3.16 (m, 2H), 3.07 (m, 1H), 2.83 (d, J=6 Hz, 2H), 2.20 (m, 2), 1.96 (m, 4H).

Ethyl 4-(5,6,7,8-tetrahydro-[1,8]naphthyridin-2-yl) piperidinyl-malonate (4-6)

A mixture of 4-5 (150 mg, 0.52 mmol), ethyl hydrogen malonate (76 mg, 0.57 mmol), HOBT (70 mg, 0.52 mmol), NMM (0.29 mL, 2.1 mmol), and DMF (4 mL) was treated with EDC (97 mg, 0.52 mmol). After 20 hr, the reaction mixture was diluted with EtOAc and then washed with sat. NaHCO₃, H₂O, and brine, dried (MgSO₄), and concentrated. Flash chromatography (silica, EtOAc) gave 4-6 as an oil.

¹H NMR (300 MHz, CDCl₃) δ7.05 (m, 1H), 6.35 (d, J=8 Hz, 1H), 4.78 (bs, 1H), 4.70 (m, 1H), 4.50 (m, 1H), 4.20 (m, 2H), 3.76 (m, 2H), 3.50 (m, 3H), 3.40 (m, 2H), 3.30 (m, 1H), 2.85–2.50 (m, 4H), 2.10–1.50 (m, 6H), 1.28 (m, 3H).

4-(5,6,7,8-Tetrahydro-[1,8]naphthyridin-2-yl) piperidinyl-malonyl-3(S)-pyridin-3-yl-β-alanine ethyl ester (4-7)

A solution of 4-6 (43 mg, 0.13 mmol), 1N NaOH (0.32 mL), THF (1 mL), and H₂O (1 mL) was stirred at ambient temperature for 1 hr. The reaction mixture was then treated with 1N HCl (0.32 mL) and concentrated to give a semi-solid. The residue was dissolved in DMF (4 mL) and treated sequentially with 1-11(37 mg, 0.14 mmol), HOBT (19 mg, 0.14 mmol), NMM (138 uL, 0.98 mmol), and EDC (27 mg, 0.14 mmol). After 20 hr, the reaction mixture was diluted with EtOAc and then washed with sat, NaHCO₃, H₂O, and brine, dried (MgSO₄), and concentrated. Flash chromatography (silica, 70:15:5 CHCl₃/methanol/EtOAc) gave 4-7 as a yellowish oil.

¹H NMR (300 MHz, CDCl₃) δ9.02 (d, J=8 Hz, 0.5H), 8.90 (d, J=8 Hz, 0.5H), 8.62 (m, 1H), 8.50 (m, 1H), 7.70 (m, 1H), 7.23 (m, 1H), 7.07 (d, J=8 Hz, 1H), 6.28 (m, 1H), 5.49 (m, 1H), 4.88 (m, 1H), 4.72 (m, 0.5 H), 4.45(m, 0.5H), 4.10 (m, 2H), 3.90 (m, 1H), 3.40 (m, 4H), 3.00–2.50 (m, 6H), 2.05–1.50 (m, 6H), 1.17 (t, J=7 Hz, 3H)

4-(5,6,7,8-Tetrahydro-[1,8]naphthyridin-2-yl) piperidinyl-malonyl-3(S)-pyridin-3-yl-β-alanine (4-8)

A mixture of 4-7 (20 mg, 42 umol), 1N NaOH (104 uL), THF (0.2 mL), and H₂O (0.2 mL) was stirred at ambient temperature for 3 hr. The reaction mixture was treated with 1N HCl (110 uL) and then concentrated. Flash Chromatography (silica, 15:15:1:1 EtOAc/ethanol/H$_2$O/NH$_4$OH) gave 4-8 as a white solid.
TLC Rf=0.15 (silica, 15:10:1:1 EtOAc/ethanol/H$_2$O/ NH$_4$OH), $^1$H NMR (300 MHz, CD$_3$OD) δ8.58 (m, 1H), 8.42 (m, 1H), 7.86 (m, 1H), 7.42 (m, 2H), 6.50 (m, 1H), 5.40 (m, 1H), 4.48 (m, 1H), 3.88 (m, 1H), 3.70–3.00 (m, 5H), 3.00–2.40 (m, 6H), 2.00–1.00 (m, 6H).
Utilizing the chemistry contained in Schemes 1-8, the following compounds 5, 6, 7 and 8 are prepared.
5
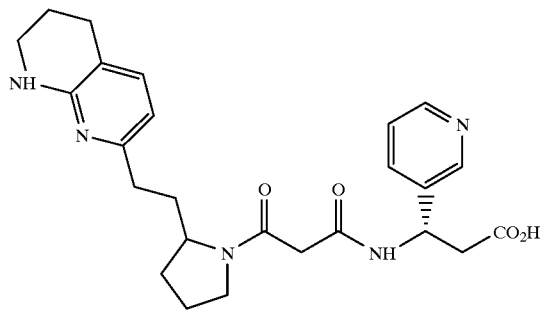
6
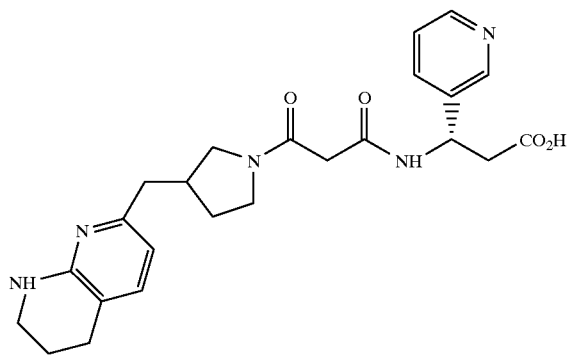
7
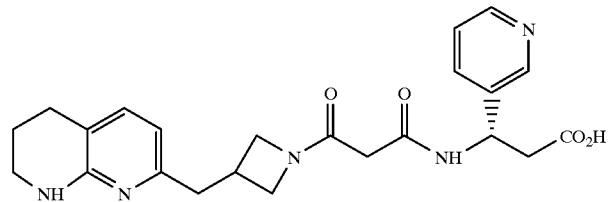
8
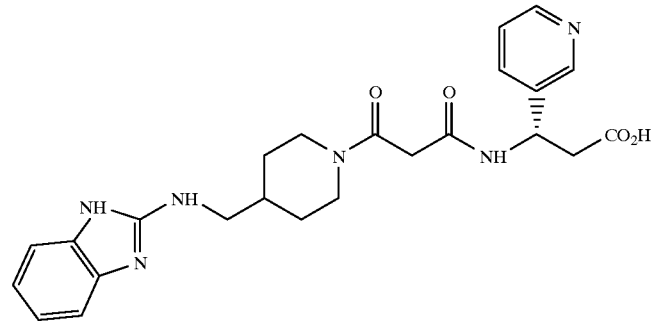

SCHEME 5
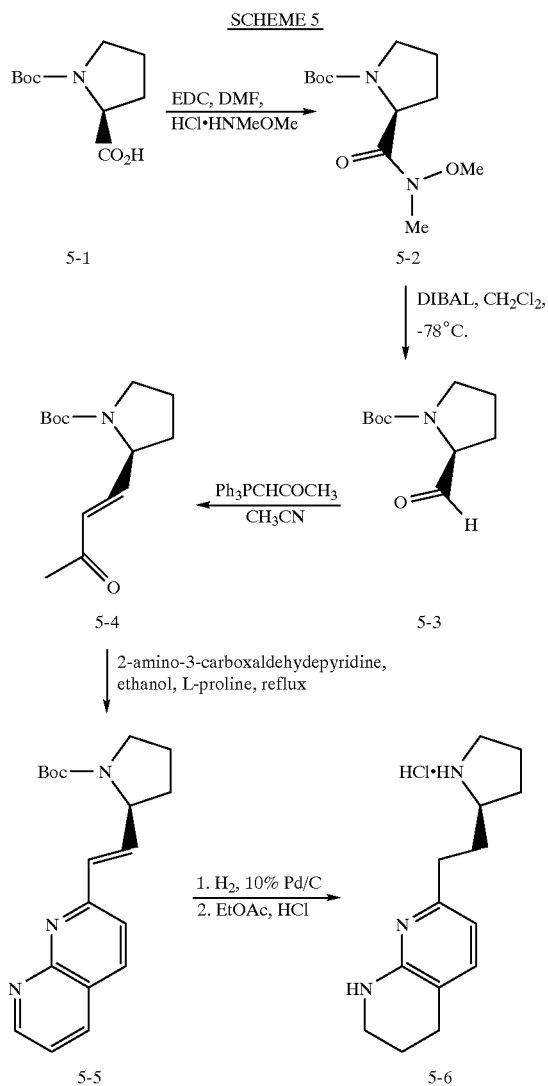
SCHEME 6
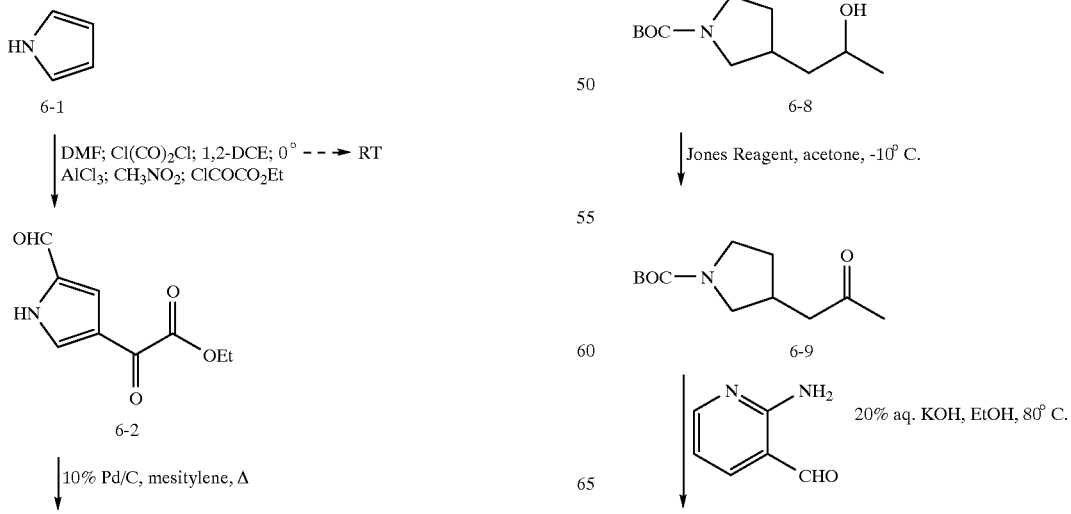
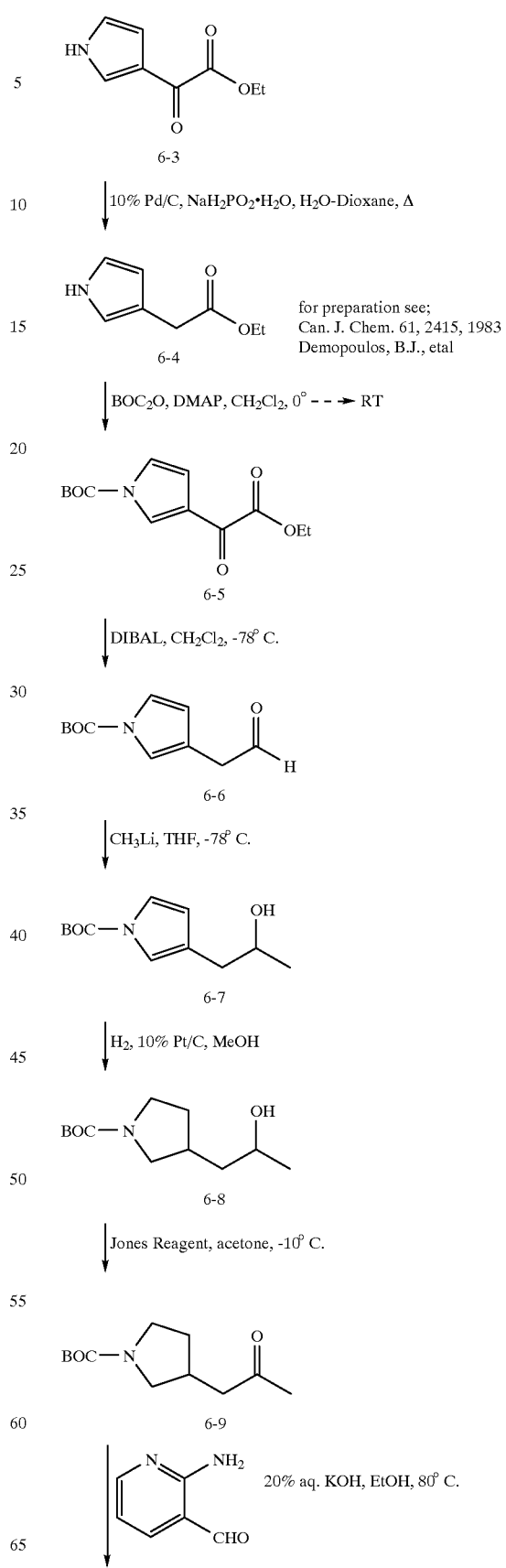

35
-continued

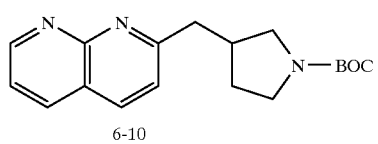
6-10

↓ H₂, 10% Pd/C, EtOAc

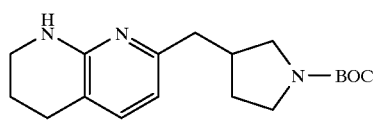
6-11

↓ 6 N HCl, Dioxane

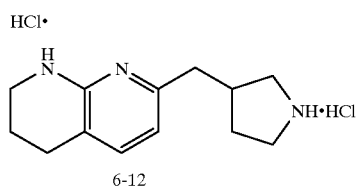
6-12

SCHEME 7

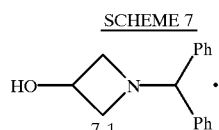
7-1 for preparation see: J. Org. Chem. 1972, 37(24), 3953-5, Anderson, A. G., et. al.

↓ Cl(CO)₂Cl, DMSO, NEt₃, CH₂Cl₂

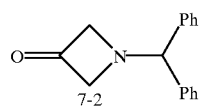
7-2

↓ a) 20% Pd(OH)₂, H₂, CH₃OH
b) BOC₂O, NEt₃, CH₂Cl₂

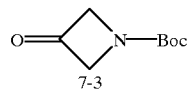
7-3

↓ Ph₃PCHCOCH₃, toluene, 60° C.

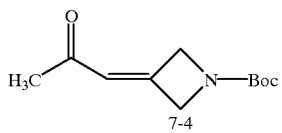
7-4

↓ 20% aqueous KOH, H₂O/dioxane, 80° C.

36
-continued

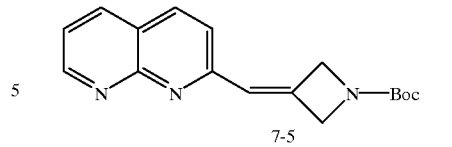
7-5

↓ a) H₂, 10% Pd/C, EtOAc
b) HCl, H₂O/dioxane

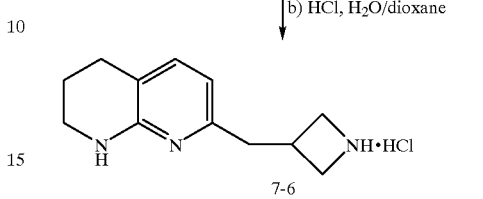
7-6

SCHEME 8

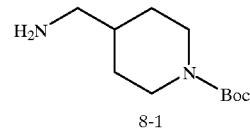
8-1 for preparation see: Synth. Commun. 1992, 22(16), 2357-2360, Prugh, J. D., et. al.

↓ 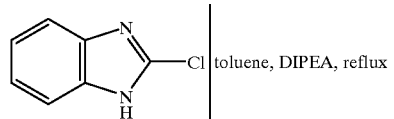 toluene, DIPEA, reflux

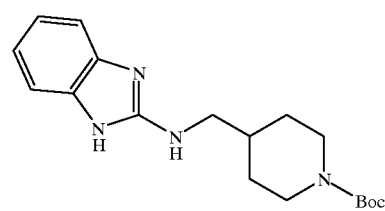
8-2

↓ HCl, EtOAc

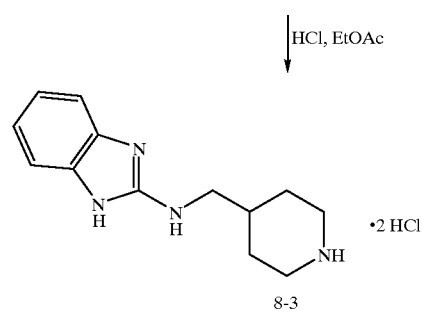
8-3

SCHEME 9

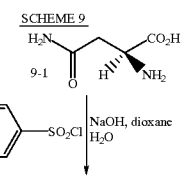
9-1

↓ NaOH, dioxane, H₂O

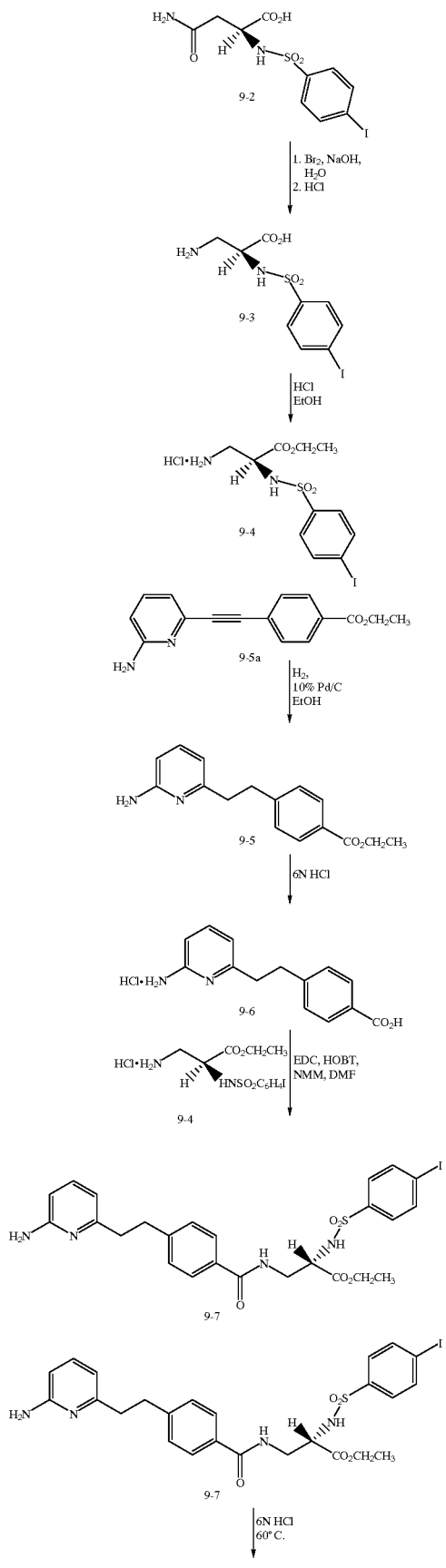
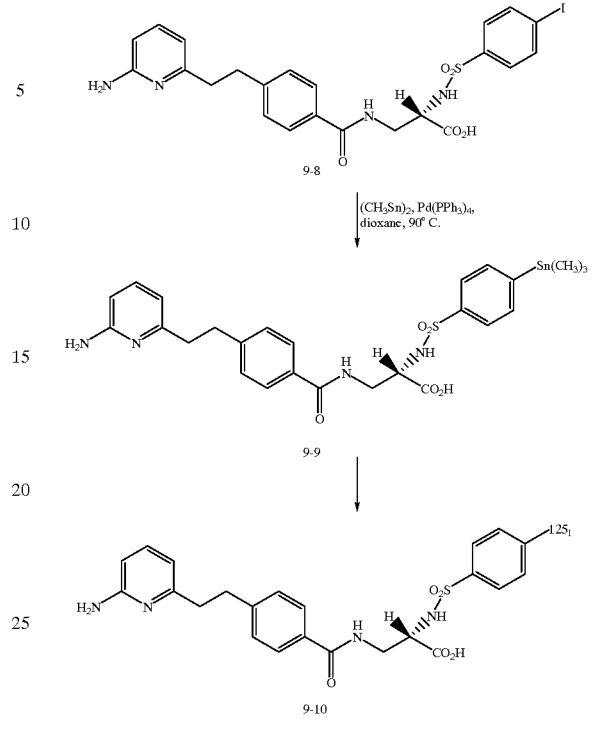

N-(4-Iodo-phenylsulfonylamino)-L-asparagine (9-2)

To a stirred solution of acid 9-1(4.39 g, 33.2 mmol), NaOH (1.49 g, 37.2 mmol), dioxane (30 ml) and H$_2$O (30 ml) at 0° C. was added pipsyl chloride (10.34 g, 34.2 mmol). After ~5 minutes, NaOH (1.49, 37.2 mmol) dissolved in 15 ml H$_2$O, was added followed by the removal of the cooling bath. After 2.0 h, the reaction mixture was concentrated. The residue was dissolved in H$_2$O (300 ml) and then washed with EtOAc. The aqueous portion was cooled to 0° C. and then acidified with concentrated HCl. The solid was collected and then washed with Et$_2$O to provide acid 9-2 as a white solid.

$^1$H NMR (300 MHz, D$_2$O) δ7.86 (d, 2H, J=8 Hz), 7.48 (d, 2H, J=8 Hz) 3.70 (m, 1H), 2.39 (m, 2H).

2(S)-(4-Iodo-phenylsulfonylamino)-β-alanine (9-3)

To a stirred solution of NaOH (7.14 g, 181.8 mmol) and H$_2$O (40 ml) at 0° C. was added Br$_2$ (1.30 ml, 24.9 mmol) dropwise over a ten minute period. After ~5 minutes, acid 9-2 (9.9 g, 24.9 mmol), NaOH (2.00 g, 49.8 mmol) and H$_2$O (35 ml) were combined, cooled to 0° C. and then added in a single portion to the reaction. After stirring for 20 minutes at 0° C., the reaction was heated to 90° C. for 30 minutes and then recooled to 0° C. The pH was adjusted to ~7 by dropwise addition of concentrated HCl. The solid was collected, washed with EtOAc, and then dried in vacuo to provide acid 9-3 as a white solid.

$^1$H NMR (300 MHz, D$_2$O) δ8.02 (d, 2H, J=8 Hz), 7.63 (d, 2H, J=8 Hz), 4.36 (m, 1H), 3.51 (dd, 1H, J=5 Hz, 13 Hz) 3.21 (m, 1H).

Ethyl 2(S)-(4-iodo-phenylsulfonylamino)-β-alanine-hydrochloride (9-4)

HCl gas was rapidly bubbled through a suspension of acid 9-3 (4.0 g, 10.81 mmol) in EtOH (50 ml) at 0° C. for 10 minutes. The cooling bath was removed and the reaction was heated to 60° C. After 18 h, the reaction was concentrated to provide ester 9-4 as a white solid.

$^1$H NMR (300 MHz, CD$_3$OD) δ7.98 (d, 2H, J=8 Hz), 7.63 (d, 2H, J=8 Hz), 4.25 (q, 1H, J=5 Hz), 3.92 (m, 2H), 3.33 (m, 1H), 3.06 (m, 1H), 1.01 (t, 3H, J=7 Hz).

Ethyl 4-[2-(2-Aminopyridin-6-yl)ethyl]benzoate (9-5)

A mixture of ester 9-5a (700 mg, 2.63 mmol), (for preparation, see: Scheme 29 of PCT International Application Publication No. WO 95/32710, published Dec. 7, 1995) 10% Pd/C (350 mg) and EtOH were stirred under 1 atm H$_2$. After 20 h, the reaction was filtered through a celite pad and then concentrated to provide ester 9-5 as a brown oil.

TLC R$_f$=0.23 (silica, 40% EtOAc/hexanes) $^1$H NMR (300 MHz, CDCl$_3$) δ7.95 (d, 2H, J=8 Hz), 7.26 (m, 3H), 6.43 (d, 1H, J=7 Hz), 6.35 (d, 1H, J=8 Hz), 4.37 (m, 4H), 3.05 (m, 2H), 2.91 (m, 2H), 1.39 (t, 3H, J=7 Hz).

4-[2-(2-Aminopyridin-6-yl)ethyl]benzoic acid hydrochloride (9-6)

A suspension of ester 9-5 (625 mg, 2.31 mmol) in 6N HCl (12 ml) was heated to 60° C. After ~20 h, the reaction was concentrated to give acid 9-6 as a tan solid.

$^1$H NMR (300 MHz, CD$_3$OD) δ7.96 (d, 2H, J=8 Hz), 7.80 (m, 1H), 7.33 (d, 2H, J=8 Hz), 6.84 (d, 1H, J=9 Hz), 6.69 (d, 1H, J=7 Hz), 3.09 (m, 4H).

Ethyl 4-[2-(2-Aminopyridin-6-yl)ethyl]benzoyl-2 (S)-(4-iodophenylsulfonylamino)-β-alanine (9-7)

A solution of acid 9-6 (400 mg, 1.43 mmol), amine 94 (686 mg, 1.57 mmol), EDC (358 mg, 1.86 mmol), HOBT (252 mg, 1.86 mmol), NMM (632 μl, 5.72 mmol) and DMF (10 ml) was stirred for ~20 h. The reaction was diluted with EtOAc and then washed with sat NaHCO$_3$, brine, dried (MgSO$_4$) and concentrated. Flash chromatography (silica, EtOAC AE 5% isopropanol/EtOAc) provided amide 9-7 as a white solid.

TLC R$_f$=0.4 (silica, 10% isopropanol/EtOAc) $^1$H NMR (300 MHz, CD$_3$OD) δ7.79 (d, 2H, J=9 Hz) 7.61 (d, 2H, J=8 Hz), 7.52 (d, 2H, J=9 Hz), 7.29 (m, 1H), 7.27 (d, 2H, J=8 Hz), 4.20 (m, 1H), 3.95 (q, 2H, J=7 Hz), 3.66 (dd, 1H, J=6 Hz, 14 Hz), 3.49 (dd, 1H, J=8Hz, 13 Hz), 3.01 (m, 2H), 2.86 (m, 2H), 1.08 (t, 3H, J=7 Hz).

4-[2-(2-Aminopyridin-6-yl)ethyl]benzoyl-2(S)-(4-iodophenylsulfonylamino)-β-alanine (9-8)

A solution of ester 9-7 (200 mg, 0.3213 mmol) and 6N HCl (30 ml) was heated to 60° C. After ~20 h, the reaction mixture was concentrated. Flash chromatography (silica, 20:20:1:1 EtOAc/EtOH/NH$_4$OH/H$_2$O) provided acid 9-8 as a white solid.

TLC R$_f$=0.45 (silica, 20:20:1:1 EtOAc/EtOH/NH$_4$OH/H$_2$O) $^1$H NMR (400 MHz, DMSO) δ8.40 (m, 1H), 8.14 (Bs, 1H), 7.81 (d, 2H, J=8 Hz), 7.62 (d, 2H, J=8 Hz), 7.48 (d, 2H, J=8 Hz), 7.27 (m, 3H), 6.34 (d, 1H, J=7 Hz), 6.25 (d, 1H, J=8 Hz), 5.85 (bs, 2H), 3.89 (bs, 1H), 3.35 (m, 2H), 2.97 (m, 2H), 2.79 (m, 2H).

4-[2-(2-Aminopyridin-6-yl)ethyl)benzoyl-2(S)-(4-trimethylstannyl-phenylsulfonylamino-β-alanine (9-9)

A solution of iodide 9-8 (70 mg, 0.1178 mmol), (CH$_3$Sn)$_2$ (49 μl, 0.2356 mmol), Pd(PPh$_3$)$_4$ (5 mg) and dioxane (7 ml) was heated to 90° C. After 2 h, the reaction was concentrated and then purified by prep HPLC (Delta-Pak C$_{18}$ 15 μM 100 A°, 40×100 mm; 95:5 AE 5:95 H$_2$O/CH$_3$CN) provided the trifluoroacetate salt. The salt was suspended in H$_2$O (10 ml), treated with NH$_4$OH (5 drops) and then lyophilized to provide amide 9-9 as a white solid.

$^1$H NMR (400 MHz, DMSO) δ8.40 (m, 1H), 8.18 (d, 1H, J=8 Hz), 7.67 (m, 5H), 7.56 (d, 2H, J=8 Hz), 7.29 (d, 2H, J=8 Hz), 6.95–7.52 (m, 2H), 6.45 (bs, 2H), 4.00 (m, 1H), 3.50 (m, 1H), 3.33 (m, 1H), 2.97 (m, 2H), 2.86 (m, 2H).

4-[2-(2-Aminopyridin-6-yl)ethyl]benzoyl-2(S)-4-$^{125}$iodophenylsulfonylamino-β-alanine (9-10)

An iodobead (Pierce) was added to a shipping vial of 5 mCi of Na$^{125}$I (Amersham, IMS30) and stirred for five minutes at room temperature. A solution of 0.1 mg of 9-9 in 0.05 mL of 10% H$_2$SO$_4$/MeOH was made and immediately added to the Na$^{125}$I/iodobead vial. After stirring for three minutes at room temperature, approximately 0.04–0.05 mL of NH$_4$OH was added so the reaction mixture was at pH 6–7. The entire reaction mixture was injected onto the HPLC for purification [Vydac peptide-protein C-18 column, 4.6×250 mm, linear gradient of 10% acetonitrile (0.1% (TFA):H$_2$O (0.1% TFA) to 90% acetonitrile (0.1% TFA):H$_2$O (0.1% TFA) over 30 minutes, 1 mL/min]. The retention time of 9-10 is 17 minutes under these conditions. Fractions containing the majority of the radioactivity were pooled, lyophilized and diluted with ethanol to give approximately 1 mCi of 9-10, which coeluted on HPLC analysis with an authentic sample of 9-8.

Instrumentation: Analytical and preparative HPLC was carried out using a Waters 600E Powerline Multi Solvent Delivery System with 0.1 mL heads with a Rheodyne 7125 injector and a Waters 990 Photodiode Array Detector with a Gilson FC203 Microfraction collector. For analytical and preparative HPLC a Vydac peptide-protein C-18 column, 4.6×250 mm was used with a C-18 Brownlee modular guard column. The acetonitrile used for the HPLC analyses was Fisher Optima grade. The HPLC radiodetector used was a Beckman 170 Radioisotope detector. A Vydac C-18 protein and peptide column, 3.9×250 mm was used for analytical and preparative HPLC. Solutions of radioactivity were concentrated using a Speedvac vacuum centrifuge. Calibration curves and chemical concentrations were determined using a Hewlett Packard Model 8452A UV/Vis Diode Array Spectrophotometer. Sample radioactivities were determined in a Packard A5530 gamma counter.

The test procedures employed to measure avb3 binding and the bone resorption inhibiting activity of the compounds of the present invention are described below.

BONE RESORPTION-PIT ASSAY

When osteoclasts engage in bone resorption, they will literally cause the formation of pits in the surface of bone that they are acting upon. Therefore, when testing compounds for their ability to inhibit osteoclasts, it is useful to measure the ability of osteoclasts to excavate these resorption pits when the inhibiting compound is present.

Consecutive 200 micron thick cross sections from a six mm cylinder of bovine femur diaphysis were cut with a low speed diamond saw (Isomet, Beuler, Ltd., Lake Bluff, Ill.). Bone slices were pooled, placed in a 10% ethanol solution and refrigerated until further use.

Prior to experimentation, bone slices were ultrasonicated twice, 20 minutes each in H$_2$O. Cleaned slices were placed in 96 well plates such that two control lanes and one lane for each drug dosage are available. Each lane represents either triplicate or quadruplicate cultures. The bone slices in 96 well plates were sterilized by UV irradiation. Prior to incubation with osteoclasts, the bone slices were hydrated by the addition of 0.1 ml Medium 199, pH 6.9 containing 15% fetal bovine serum and 1% penicillin/streptomycin.

Osteoclasts were isolated from the long bones of 1 to 3 day old rat pups (Sprague-Dawley) by modifications of Chambers et al., (*J. Cell. Science*, 66:383–399). The resulting suspension (0.75 ml/bone) was gently triturated 90–120 times using a wide bore transfer pipet. The cellular population was separated from bone fragments by a cell strainer with a 100 micron nylon mesh. 100 μl of the cell suspension was placed onto each bone slice. Test compounds were then added at the desired experimental concentrations.

Bone slices exposed to osteoclasts for 20–24 hrs were processed for staining. Tissue culture media was removed from each bone slice. Each well was washed with 200 μl of $H_2O$, and the bone slices were then fixed for 20 minutes in 2.5% glutaraldehyde, 0.1 M cacodylate, pH 7.4. After fixation, any remaining cellular debris was removed by 2 min. ultrasonication in the presence of 0.25 M $NH_4OH$ followed by 2×15 min ultrasonication in $H_2O$. The bone slices were immediately stained for 6–8 min with filtered 1% toluidine blue and 1% borax.

After the bone slices have dried, resorption pits were counted in test and control slices. Resorption pits were viewed in a Microphot Fx (Nikon) fluorescence microscope using a polarizing Nikon IGS filter cube. Test dosage results were compared with controls and resulting $IC_{50}$ values were determined for each compound tested.

The appropriateness of extrapolating data from this assay to utility and use in mammalian (including human) disease states is supported by the teaching found in Sato, M., et al., *Journal of Bone and Mineral Research*, Vol. 5, No. 1, 1990. That article teaches that certain bisphosphonates have been used clinically and appear to be effective in the treatment of Paget's disease, hypercalcemia of malignancy, osteolytic lesions produced by bone metastases, and bone loss due to immobilization or sex hormone deficiency. These same bisphosphonates are then tested in the resorption pit assay described above to confirm a correlation between their known utility and positive performance in the assay.

EIB ASSAY

Duong et al., *J. Bone Miner. Res.*, 8:S 378, describe a system for expressing the human integrin αvβ3. It has been suggested that the integrin stimulates attachment of osteoclasts to bone matrix, since antibodies against the integrin, or RGD-containing molecules, such as echistatin (European Publication 382 451), can effectively block bone resorption.
Reaction Mixture:
1. 175 μl TBS buffer (50 mM Tris.HCl pH 7.2, 150 mM NaCl, 1% BSA, 1 mM $CaCl_2$, 1 mM $MgCl_2$).
2. 25 μl cell extract (dilute with 100 mM octylglucoside buffer to give 2000 cpm/25 μl).
3. $^{125}$I-echistatin (25 μl/50,000 cpm) (see EP 382 451).
4. 25 μl buffer (total binding) or unlabeled echistatin (non-specific binding).

The reaction mixture was then incubated for 1 h at room temp. The unbound and the bound αvβ3 were separated by filtration using a Skatron Cell Harvester. The filters (prewet in 1.5% poly-ethyleneimine for 10 mins) were then washed with the wash buffer (50 mM Tris HCl, 1 mM $CaCl_2/MgCl_2$, pH 7.2). The filter was then counted in a gamma counter.

SPA ASSAY

Materials:
1. Wheatgerm agglutinin Scintillation Proximity Beads (SPA): Amersham
2. Octylglucopyranoside: Calbiochem
3. HEPES: Calbiochein
4. NaCl: Fisher
5. $CaCl_2$: Fisher
6. $MgCl_2$: SIGMA
7. Phenylmethylsulfonylfluoride (PMSF): SIGMA
8. Optiplate: PACKARD
9. 9-10 (specific activity 500–1000 Ci/mmole)
10. test compound
11. Purified integrin receptor: αvβ3 was purified from 293 cells overexpressing αvβ3 (Duong et al., *J. Bone Min. Res.*, 8:S378, 1993) according to Pytela (*Methods in Enzymology*, 144:475, 1987)
12. Binding buffer: 50 mM HEPES, pH 7.8, 100 mM NaCl, 1 mM $Ca^{2+}/Mg^{2+}$, 0.5 mM PMSF
13. 50 mM octylglucoside in binding buffer: 50-OG buffer
Procedure:
1. Pretreatment of SPA beads:
   500 mg of lyophilized SPA beads were first washed four times with 200 ml of 50-OG buffer and once with 100 ml of binding buffer, and then resuspended in 12.5 ml of binding buffer.
2. Preparation of SPA beads and receptor mixture
   In each assay tube, 2.5 μl (40 mg/ml) of pretreated beads were suspended in 97.5 μl of binding buffer and 20 ml of 50-OG buffer. 5 μl (~30 ng/ml) of purified receptor was added to the beads in suspension with stirring at room temperature for 30 minutes. The mixture was then centrifuged at 2,500 rpm in a Beckman GPR Benchtop centrifuge for 10 minutes at 4° C. The pellets were then resuspended in 50 μl of binding buffer and 25 μl of 50-OG buffer.
3. Reaction
The following were sequentially added into Optiplate in corresponding wells:
(i) Receptor/beads mixture (75 μl)
(ii) 25 μl of each of the following: compound to be tested, binding buffer for total binding or 9-8 for non-specific binding (final concentration 1 μM)
(iii) 9-10 in binding buffer (25 μl, final concentration 40 pM)
(iv) Binding buffer (125 μl)
(v) Each plate was sealed with plate sealer from PACKARD and incubated overnight with rocking at 4° C.
4. Plates were counted using PACKARD TOPCOUNT
5. 1% inhibition was calculated as follows:
   A=total counts
   B=nonspecific counts
   C=sample counts
   % inhibition=[{(A-B)-(C-B)}/(A-B)]/(A-B)×100

OCFORM ASSAY

Osteoblast-like cells (1.8 cells), originally derived from mouse calvaria, were plated in CORNING 24 well tissue culture plates in a MEM medium containing ribo- and deoxyribonucleosides, 10% fetal bovine serum and penicillin-streptomycin. Cells were seeded at 40,000/well in the morning. In the afternoon, bone marrow cells were prepared from six week old male Balb/C mice as follows:

Mice were sacrificed, tibiae removed and placed in the above medium. The ends were cut off and the marrow was flushed out of the cavity into a tube with a 1 mL syringe with a 27.5 gauge needle. The marrow was suspended by pipetting up and down. The suspension was passed through >100 µm nylon cell strainer. The resulting suspension was centrifuged at 350×g for seven minutes. The pellet was resuspended, and a sample was diluted in 2% acetic acid to lyse the red cells. The remaining cells were counted in a hemacytometer. The cells were pelleted and resuspended at $1\times10^6$ cells/mL. 50 µL was added to each well of 1.8 cells to yield 50,000 cells/well and 1,25-dihydroxy-vitamin $D_3(D_3)$ was added to each well to a final concentration of 10 nM. The cultures were incubated at 37° C. in a humidified, 5% $CO_2$ atmosphere. After 48 h, the medium was changed. 72 h after the addition of bone marrow, test compounds were added with fresh medium containing $D_3$ to quadruplicate wells. Compounds were added again after 48 h with fresh medium containing $D_3$. After an additional 48 h the medium was removed, cells were fixed with 10% formaldehyde in phosphate buffered saline for 10 minutes at room temperature, followed by a 1–2 minute treatment with ethanol:acetone (1:1) and air dried. The cells were then stained for tartrate resistant acid phosphatase as follows:

The cells were stained for 10–15 minutes at room temperature with 50 mM acetate buffer, pH 5.0 containing 30 mM sodium tartrate, 0.3 mg/mL Fast Red Violet LB Salt and 0.1 mg/mL Naphthol AS -MX phosphate. After staining, the plates were washed extensively with deionized water and air dried. The number of multinucleated, positive staining cells were counted in each well.

Representative compounds of the present invention were tested and found to bind to human αvβ3 integrin. These compounds were found to have $IC_{50}$ values in the range of 1.0 to 10,000 nM in the SPA assay.

EXAMPLE OF A PHARMACEUTICAL FORMULATION

As a specific embodiment of an oral composition, 100 mg of compound 1-13 is formulated with sufficient finely divided lactose to provide a total amount of 580 to 590 mg to fill a size O hard gel capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:
1. A compound of the formula

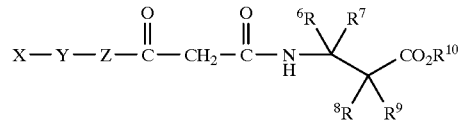

wherein X is selected from
a 5- or 6-membered monocyclic aromatic or nonaromatic ring system containing 1, 2, 3 or 4 heteroatoms selected from N, O or S wherein the 5- or 6-membered ring system is either unsubstituted or substituted with $R^1$ and $R^2$, or
a 9- to 10-membered polycyclic ring system, wherein one or more of the rings is aromatic, and wherein the polycyclic ring system contains 1, 2, 3 or 4 heteroatoms selected from N, O or S, and wherein the polycyclic ring system is either unsubstituted or substituted with $R^1$ and $R^2$;

Y is selected from

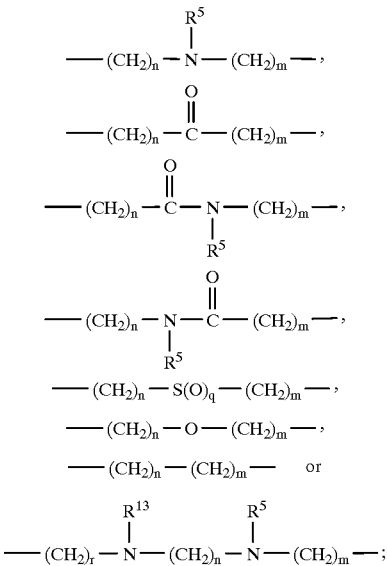

Z is absent or is a 4–11 membered aromatic or nonaromatic mono- or polycyclic ring system containing 0 to 6 double bonds, and containing 0 to 6 heteroatoms chosen from N, O and S, and wherein the ring system is either unsubstituted or substituted on a carbon or nitrogen atom with one or more groups independently selected from $R^{14}$, $R^{15}$, $R^{16}$ and $R^{17}$;

$R^1$, $R^2$, $R^3$, $R^4$, $R^5$, $R^{11}$, $R^{12}$, $R^{13}$, $R^{16}$ and $R^{17}$ are each independently selected from
hydrogen, halogen, $C_{1-10}$ alkyl, $C_{3-8}$ cycloalkyl, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy or hydroxy $C_{1-6}$ alkyl;

$R_6$, $R^7$, $R^{14}$ and $R^{15}$ are each independently selected from hydrogen, aryl,
halogen,
aryl-$(CH_2)_p$—,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
$HC\equiv C(CH_2)_r$—
$C_{1-6}$ alkyl-$C\equiv C(CH_2)_r$—,
$C_{3-7}$ cycloalkyl-$C\equiv C(CH_2)_r$—,
aryl-$C\equiv C(CH_2)_r$—,
$C_{1-6}$ alkylaryl-$C\equiv C(CH_2)_r$—,
$H_2C=CH(CH_2)_r$—,
$C_{1-6}$ alkyl-$CH=CH(CH_2)_r$—,
$C_{3-7}$ cycloalkyl-$CH=CH(CH_2)_r$—,
aryl-$CH=CH(CH_2)_r$—,
$C_{1-6}$ alkylaryl-$CH=CH(CH_2)_r$—,
$C_{1-6}$ alkyl-$SO_2(CH_2)_r$—,
$C_{1-6}$ alkylaryl-$SO_2(CH_2)_r$—,
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl, or
aryl $C_{1-8}$ alkylaminocarbonyl $C_{1-6}$ alkyl,
wherein any of the alkyl groups may be unsubstituted or substituted with $R^{11}$ and $R^{12}$; and provided that the carbon atom to which $R^6$ and $R^7$ are attached is itself attached to no more than one heteroatom; or $R^6$ and $R^7$, or $R^{14}$ and $R^{15}$ are combined to form oxo;

$R^8$ and R9 are each independently selected from
hydrogen,
aryl,
halogen,
aryl-$(CH_2)_p$—,
hydroxyl,
$C_{1-8}$ alkylcarbonylamino,
aryl $C_{1-5}$ alkoxy,
$C_{1-5}$ alkoxycarbonyl,
aminocarbonyl,
$C_{1-8}$ alkylaminocarbonyl,
$C_{1-6}$ alkylcarbonyloxy,
$C_{3-8}$ cycloalkyl,
amino,
$C_{1-6}$ alkylamino,
amino $C_{1-6}$ alkyl,
arylaminocarbonyl,
aryl $C_{1-5}$ alkylaminocarbonyl,
aminocarbonyl,
aminocarbonyl $C_{1-6}$ alkyl,
hydroxycarbonyl,
hydroxycarbonyl $C_{1-6}$ alkyl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl,
HC≡C(CH$_2$)$_r$—,
$C_{1-6}$ alkyl-C≡C(CH$_2$)$_r$—,
$C_{3-7}$ cycloalkyl-C≡C(CH$_2$)$_r$—,
aryl-C≡C(CH$_2$)$_r$—,
$C_{1-6}$ alkylaryl-C≡C(CH$_2$)$_r$—,
H$_2$C=CH(CH$_2$)$_r$—,
$C_{1-6}$ alkyl-CH=CH(CH$_2$)$_r$—,
$C_{3-7}$ cycloalkyl-CH=CH(CH$_2$)$_r$—,
aryl-CH=CH(CH$_2$)$_r$—,
$C_{1-6}$ alkylaryl-CH=CH(CH$_2$)$_r$—,
$C_{1-6}$ alkyl-SO$_2$(CH$_2$)$_r$—,
$C_{1-6}$ alkylaryl-SO$_2$(CH$_2$)$_r$—,
$C_{1-6}$ alkoxy,
aryl $C_{1-6}$ alkoxy,
aryl $C_{1-6}$ alkyl,
$C_{1-6}$ alkylamino $C_{1-6}$ alkyl,
arylamino,
arylamino $C_{1-6}$ alkyl,
aryl $C_{1-6}$ alkylamino,
aryl $C_{1-6}$ alkylamino $C_{1-6}$ alkyl,
arylcarbonyloxy,
aryl $C_{1-6}$ alkylcarbonyloxy,
$C_{1-6}$ dialkylamino,
$C_{1-6}$ dialkylamino $C_{1-6}$ alkyl,
$C_{1-6}$ alkylaminocarbonyloxy,
$C_{1-8}$ alkylsulfonylamino,
$C_{1-8}$ alkylsulfonylamino $C_{1-6}$ alkyl,
arylsulfonylamino $C_{1-6}$ alkyl,
aryl $C_{1-6}$ alkylsulfonylamino,
aryl $C_{1-6}$ alkylsulfonylamino $C_{1-6}$ alkyl,
$C_{1-8}$ alkoxycarbonylamino,
$C_{1-8}$ alkoxycarbonylamino $C_{1-8}$ alkyl,
aryloxycarbonylamino $C_{1-8}$ alkyl,
aryl $C_{1-8}$ alkoxycarbonylamino,
aryl $C_{1-8}$ alkoxycarbonylamino $C_{1-8}$ alkyl,
$C_{1-8}$ alkylcarbonylamino,
$C_{1-8}$ alkylcarbonylamino $C_{1-6}$ alkyl,
arylcarbonylamino $C_{1-6}$ alkyl,
aryl $C_{1-6}$ alkylcarbonylamino,
aryl $C_{1-6}$ alkylcarbonylamino $C_{1-6}$ alkyl,
aminocarbonylamino $C_{1-6}$ alkyl,
$C_{1-8}$ alkylaminocarbonylamino,
$C_{1-8}$ alkylaminocarbonylamino $C_{1-6}$ alkyl,
arylaminocarbonylamino $C_{1-6}$ alkyl,
aryl $C_{1-8}$ alkylaminocarbonylamino,
aryl $C_{1-8}$ alkylaminocarbonylamino $C_{1-6}$ alkyl,
aminosulfonylamino $C_{1-6}$ alkyl,
$C_{1-8}$ alkylaminosulfonylamino,
$C_{1-8}$ alkylaminosulfonylamino $C_{1-6}$ alkyl,
arylaminosulfonylamino $C_{1-6}$ alkyl,
aryl $C_{1-8}$ alkylaminosulfonylamino,
aryl $C_{1-8}$ alkylaminosulfonylamino $C_{1-6}$ alkyl,
$C_{1-6}$ alkylsulfonyl,
$C_{1-6}$ alkylsulfonyl $C_{1-6}$ alkyl,
arylsulfonyl $C_{1-6}$ alkyl,
aryl $C_{1-6}$ alkylsulfonyl,
aryl $C_{1-6}$ alkylsulfonyl $C_{1-6}$ alkyl,
$C_{1-6}$ alkylcarbonyl,
$C_{1-6}$ alkylcarbonyl $C_{1-6}$ alkyl,
arylcarbonyl $C_{1-6}$ alkyl,
aryl $C_{1-6}$ alkylcarbonyl,
aryl $C_{1-6}$ alkylcarbonyl $C_{1-6}$ alkyl,
$C_{1-6}$ alkylthiocarbonylamino,
$C_{1-6}$ alkylthiocarbonylamino $C_{1-6}$ alkyl,
arylthiocarbonylamino $C_{1-6}$ alkyl,
aryl $C_{1-6}$ alkylthiocarbonylamino,
aryl $C_{1-6}$ alkylthiocarbonylamino $C_{1-6}$ alkyl,
$C_{1-8}$ alkylaminocarbonyl $C_{1-6}$ alkyl,
arylaminocarbonyl $C_{1-6}$ alkyl,
aryl $C_{1-8}$ alkylaminocarbonyl,
aryl $C_{1-8}$ alkylaminocarbonyl $C_{1-6}$ alkyl,
$C_{7-20}$ polycyclyl $C_{0-8}$ alkylsulfonylamino $C_{0-6}$ alkyl,
$C_{7-20}$ polycyclyl $C_{0-8}$ alkylcarbonylamino $C_{0-6}$ alkyl,
$C_{7-20}$ polycyclyl $C_{0-8}$ alkylaminosulfonylamino $C_{0-6}$ alkyl,
$C_{7-20}$ polycyclyl $C_{0-8}$ alkylaminocarbonylamino $C_{0-6}$ alkyl, or
$C_{7-20}$ polycyclyl $C_{0-8}$ alkyloxycarbonylamino $C_{0-6}$ alkyl wherein any of the alkyl groups may be unsubstituted or substituted with $R^{11}$ and $R^{12}$, wherein any of the polycyclyl may be unsubstituted or substituted with $R^{18}$, $R^{19}$, $R^{20}$ and $R^{21}$, and provided that the carbon atom to which $R^8$ and $R^9$ are attached is itself attached to no more than one heteroatom; or $R^8$ and $R^9$ are combined to form oxo;

$R^{10}$ is selected from
hydrogen,
$C_{1-8}$ alkyl,
aryl,
aryl $C_{1-8}$ alkyl,
aryl $C_{1-6}$ alkoxy,
$C_{1-8}$ alkylcarbonyloxy $C_{1-4}$ alkyl,
aryl $C_{1-8}$ alkylcarbonyloxy $C_{1-4}$ alkyl,
$C_{1-8}$ alkylaminocarbonylmethylene, or
$C_{1-8}$ dialkylaminocarbonylmethylene;

$R^{18}$, $R^{19}$, $R^{20}$ and $R^{21}$ are each independently selected from
hydrogen, halogen, $C_{1-10}$ alkyl, $C_{3-8}$ cycloalkyl, oxo, aryl, aryl $C_{1-8}$ alkyl, amino, amino $C_{1-8}$ alkyl, $C_{1-3}$ acylamino, $C_{1-3}$ acylamino $C_{1-8}$ alkyl, $C_{1-6}$ alkylamino, $C_{1-6}$ alkylamino-$C_{1-8}$ alkyl, $C_{1-6}$ dialkylamino, $C_{1-6}$ dialkylamino $C_{1-8}$ alkyl, $C_{1-4}$ alkoxy, $C_{1-4}$ alkoxy $C_{1-6}$ alkyl, hydroxycarbonyl, hydroxycarbonyl $C_{1-6}$ alkyl, $C_{1-3}$ alkoxycarbonyl, $C_{1-3}$ alkoxycarbonyl $C_{1-6}$ alkyl, hydroxycarbonyl-$C_{1-6}$ alkyloxy, hydroxy, hydroxy $C_{1-6}$ alkyl, $C_{1-6}$ alkyloxy-$C_{1-6}$ alkyl, nitro, cyano, trifluoromethyl, trifluoromethoxy, trifluoroethoxy, $C_{1-8}$ alkyl-S(O)$_q$, $C_{1-8}$ alkylaminocarbonyl, $C_{1-8}$ dialkylaminocarbonyl, $C_{1-8}$ alkyloxycarbonylamino, $C_{1-8}$ alkylaminocarbonyloxy or $C_{1-8}$alkylsulfonylamino;

m, n and r are each independently an integer from 0 to 3;
p is an integer from 1 to 4; and
q is an integer from 0 to 2;
and the pharmaceutically acceptable salts thereof.

2. The compound of claim 1, wherein

X is
a 9- to 10-membered polycyclic ring system, wherein one or more of the rings is aromatic, and wherein the polycyclic ring system contains 1, 2, 3 or 4 heteroatoms selected from N, O or S, and wherein the polycyclic ring system is either unsubstituted or substituted with $R^1$ and $R^2$; and and the pharmaceutically acceptable salts thereof.

3. The compound of claim 2 wherein the compound has the formula $$X-Y-Z-\overset{O}{\underset{\|}{C}}-CH_2-\overset{O}{\underset{\|}{C}}-\underset{H}{N}-\overset{R^6}{\underset{|}{C}}H-CO_2R^{10}$$

wherein X is selected from

[structures: tetrahydronaphthyridine variants with $R^1$, $R^2$; and benzimidazole with $R^1$];

Z is absent or is selected from

[structures of various N-containing heterocycles with $R^{14}$, $R^{15}$, $R^{16}$ substituents, including piperazines, bicyclic amines, isoxazoles, pyrroles, etc.];

$R^6$ is selected from hydrogen,
aryl,
—$(CH_2)_p$-aryl,
$C_{1-8}$ alkyl, either unsubstituted or substituted, with one or more groups selected from: halogen, hydroxyl, $C_{1-5}$ alkylcarbonylamino, aryl $C_{1-5}$ alkoxy, $C_{1-5}$ alkoxycarbonyl, aminocarbonyl, $C_{1-5}$ alkylaminocarbonyl, $C_{1-5}$ alkylcarbonyloxy, $C_{3-8}$ cycloalkyl, oxo, amino, $C_{1-3}$ alkylamino, amino $C_{1-3}$ alkyl, arylaminocarbonyl, aryl $C_{1-5}$ alkylaminocarbonyl, aminocarbonyl, aminocarbonyl $C_{1-4}$ alkyl, hydroxycarbonyl, or hydroxycarbonyl $C_{1-5}$ alkyl, HC≡C($CH_2$)$_r$—
$C_{1-6}$ alkyl-C≡C($CH_2$)$_r$—,
$C_{3-7}$ cycloalkyl-C≡C($CH_2$)$_r$—,
aryl-C≡C($CH_2$)$_r$—,
$C_{1-6}$ alkylaryl-C≡C($CH_2$)$_r$—,
$H_2$C=CH($CH_2$)$_r$—,
$C_{1-6}$ alkyl-CH=CH($CH_2$)$_r$—,
$C_{3-7}$ cycloalkyl-CH=CH($CH_2$)$_r$—,
aryl-CH=CH($CH_2$)$_r$—,
$C_{1-6}$ alkylaryl-CH=CH($CH_2$)$_r$—,
$C_{1-6}$ alkyl-SO$_2$($CH_2$)$_r$—, or
$C_{1-6}$ alkylaryl-SO$_2$($CH_2$)$_r$—, and the pharmaceutically acceptable salts thereof.

4. The compound of claim 3 of the formula $$X-Y-Z-\overset{O}{\underset{\|}{C}}-CH_2-\overset{O}{\underset{\|}{C}}NH-\overset{R^6}{\underset{\vdots}{C}}\overset{H}{\triangleleft}-CO_2R^{10}$$

wherein Y is selected from $$-\underset{\underset{R^5}{|}}{N}-(CH_2)_m- \quad \text{or} \quad -(CH_2)_m-;$$

Z is absent or is selected from

[structures: azetidine, pyrrolidine, piperidine N-methyl variants with $R^{16}$];

$R^6$ is selected from
hydrogen,

[phenyl, pyridyl structures],

—$(CH_2)_p$ indolyl,
HC≡C($CH_2$)$_r$—
$C_{1-6}$ alkyl-C≡C($CH_2$)$_r$—,
$C_{3-7}$ cycloalkyl-C≡C($CH_2$)$_r$—,
aryl-C≡C($CH_2$)$_r$—, $C_{1-6}$ alkylaryl-C≡C(CH$_2$)$_r$—,
H$_2$C=CH(CH$_2$)$_r$—,
$C_{1-6}$ alkyl-CH=CH(CH$_2$)$_r$—,
$C_{3-7}$ cycloalkyl-CH=CH(CH$_2$)$_r$—,
aryl-CH=CH(CH$_2$)$_r$—,
$C_{1-6}$ alkylaryl-CH=CH(CH$_2$)$_r$—,
$C_{1-6}$ alkyl-SO$_2$(CH$_2$)$_r$—, or
$C_{1-6}$ alkylaryl-SO$_2$(CH$_2$)$_r$—; and
R$^{10}$ is selected from hydrogen or $C_{1-8}$ alkyl;
and the pharmaceutically acceptable salts thereof.

5. The compound of claim 4 selected from
Ethyl 3(S)-pyridin-3-yl-3-{2-[3-(5,6,7,8-tetrahydro-[1,8]naphthyridin-2-yl)propylcarbamoyl]acelamino}propionate;
3(S)-pyridin-3-yl-3-{2-[3-(5,6,7,8-tetrahydro-[1,8]naphthyridin-2-5 yl)propylcarbamoyl]acetylamino}propionic acid;
3-(5,6,7,8-Tetrahydro-[1,8]naphthyridin-2-ylmethyl)piperidinyl-malonyl-3(S)-pyridin-3-yl-β-alanine ethyl ester;
3-(5,6,7,8-Tetrahydro-[1,8]naphthyridin-2-ylmethyl)piperidinyl-malonyl-3(S)-pyridin-3-yl-β-alanine;
4-(5,6,7,8-Tetrahydro-[1,8]naphthyridin-2-ylmethyl)piperidinyl-malonyl-3(S)-pyridin-3-yl-β-alanine ethyl ester;
4-(5,6,7,8-Tetrahydro-[1,8]naphthyridin-2-ylmethyl)piperidinyl-malonyl-3(S)-pyridin-3-yl-β-alanine;
4-(5,6,7,8-Tetrahydro-[1,8]naphthyridin-2-yl)piperidinyl-malonyl-3(S)-pyridin-3-yl-β-alanine ethyl ester; or
4-(5,6,7,8-Tetrahydro-[1,8]naphthyridin-2-yl)piperidinyl-malonyl-3(S)-pyridin-3-yl-β-alanine;
and the pharmaceutically acceptable salts thereof.

6. The compound of claim 5 selected from
3(S)-Pyridin-3-yl-3-{2-[3-(5,6,7,8-tetrahydro-[1,8]naphthyridin-2-yl)propylcarbamoyl]acetylamino}propionic acid;
3-(5,6,7,8-Tetrahydro-[1,8]naphthyridin-2-ylmethyl)piperidinyl-malonyl-3(S)-pyridin-3-yl-β-alanine;
4-(5,6,7,8-Tetrahydro-[1,8]naphthyridin-2-ylmethyl)piperidinyl-malonyl-3(S)-pyridin-3-yl-β-alanine; or
4-(5,6,7,8-Tetrahydro-[1,8]naphthyridin-2-yl)piperidinyl-malonyl-3(S)-pyridin-3-yl-β-alanine;
and the pharmaceutically acceptable salts thereof.

7. A pharmaceutical composition comprising the compound of claim 1 and a pharmaceutically acceptable carrier.

8. A process for making a pharmaceutical composition comprising combining a compound of claim 1 and a pharmaceutically acceptable carrier.

9. A method of eliciting a vitronectin antagonizing effect in a mammal in need thereof, comprising administering to the mammal a therapeutically effective amount of the compound of claim 1.

10. The method of claim 9, wherein the vitronectin antagonizing effect is selected from inhibition of bone resorption, inhibition of restenosis, inhibition of angiogenesis, inhibition of diabetic retinopathy, inhibition of macular degeneration or inhibition of tumor growth.

11. The method of claim 10, wherein the vitronectin antagonizing effect is the inhibition of bone resorption.

12. A method of treating or preventing a condition mediated by antagonism of a vitronectin receptor in a mammal in need thereof, comprising administering to the mammal a therapeutically effective amount of the compound of claim 1.

13. The method of claim 12, wherein the condition is elected from the group consisting of osteoporosis and cancer.

14. The method of claim 13, wherein the condition is steoporosis.

15. A method of inhibiting bone resorption in a mammal in need thereof, comprising administering to the mammal a therapeutically effective amount of the compound of claim 1.

16. A method of treating osteoporosis in a mammal in need thereof, comprising administering to the mammal a therapeutically effective amount of the compound of claim 1.

17. A method of preventing osteoporosis in a mammal in need thereof, comprising administering to the mammal a therapeutically effective amount of the compound of claim 1.

18. A method of eliciting a vitronectin antagonizing effect in a mammal in need thereof, comprising administering to the mammal a therapeutically effective amount of the composition of claim 7.

19. A method of treating or preventing a condition mediated by antagonism of a vitronectin receptor in a mammal in need thereof, comprising administering to the mammal a therapeutically effective amount of the composition of claim 7.

20. A method of inhibiting bone resorption in a mammal in need thereof, comprising administering to the mammal a therapeutically effective amount of the composition of claim 7.

21. A method of treating osteoporosis in a mammal in need thereof, comprising administering to the mammal a therapeutically effective amount of the composition of claim 7.

22. A method of preventing osteoporosis in a mammal in need thereof, comprising administering to the mammal a therapeutically effective amount of the composition of claim 7.

23. A method of treating tumor growth in a mammal in need thereof, comprising administering to the mammal a therapeutically effective amount of a compound of claim 1 and one or more agents known to be cytotoxic or antiproliferative.

* * * * *